United States Patent [19]

Haber et al.

[11] Patent Number: 5,675,062
[45] Date of Patent: Oct. 7, 1997

[54] CELLULAR BASIS OF TRANSPLANT ARTERIOSCLEROSIS IN MICE

[75] Inventors: Edgar Haber, Salisbury, N.H.; Chengwei Shi, Allston; Wen-Sen Lee, Brookline, both of Mass.

[73] Assignee: President and Fellows of Harvard College, Cambridge, Mass.

[21] Appl. No.: 377,305

[22] Filed: Jan. 24, 1995

Related U.S. Application Data

[63] Continuation-in-part of Ser. No. 277,489, Jul. 18, 1994, abandoned.
[51] Int. Cl.$^6$ .................. C12N 15/00; A01N 1/02; A61N 5/00; A61F 2/04
[52] U.S. Cl. .................. 800/2; 435/1; 424/9.2; 424/569; 600/36; 600/1
[58] Field of Search .................. 800/2, DIG. 5, 800/DIG. 2; 424/9.2, 569; 435/1, 7.2, 961; 600/36; 623/1

[56] References Cited

FOREIGN PATENT DOCUMENTS 0 394 827 A1 10/1990 European Pat. Off. .

OTHER PUBLICATIONS

Shi et al., Circulation Research, "Murine Model of Accelerated Transplant Arteriosclerosis", issued Aug. 1994 vol. 75 No. 2, pp. 199–207.
Isobe et al., Circulation, "Imaging the Rejecting Heart: In Vivo Detection of Major Histocompatibility Complex Class II Antigen Induction", issued Feb. 1992, vol. 85, No. 2, pp. 738–746.
Raisanen–Sokolowski et al., Transplantation, "Partial Inhibition of Allograft Arteriosclerosis (Chronic Rejection) by 15–Deoxyspergualin", issued Jun. 1994, vol. 57, No. 12, pp. 1772–1777.
Hirata et al., The Journal of Heart and Lung Transplantation, "Reduction of Transplant Arteriosclerosis with Long Term Administration of 15–Deoxyspergualin", issued Jan. 1994, vol. 13, No. 1 p. S41, col. 2, abstract 39.
PCT Search Report, PCT/US95/05074, mailed 2 Aug. 1995.
Brieland et al., "Expression of Monocyte Chemoattractant Protein–1 (MCP–1) by Rat Alveolar Macrophages during Chronic Lung Injury", 1993, *Am. J. Respiratory Cell & Molec. Biol.*, 9:300–305.
Chen et al., "Intracellular Antibodies as a New Class of Therapeutic Molecules for Gene Therapy", 1994, *Human Gene Therapy*, 5:595–601.
Czubayko et al., "Ribozyme–targeting Elucidates a Direct Role of Pleiotrophin in Tumor Growth", 1994, *J. Biol. Chemistry*, 269:21358–63.
Deen et al., "A Soluble Form of CD4 (T4) Protein Inhibits AIDS Virus Infection", 1988, *Nature*, 331:82–84.

Fisher et al., "HIV Infection is Blocked in vitro by Recombinant Soluble CD4", 1988, *Nature*, 331:76–86.
Grusby et al., "Mice Lacking Major Histocompatibility Complex Class I and Class II Molecules", *Proc. Natl. Acad. Sci. USA*, 90:3913–17.
Hussey et al., "A Soluble CD4 Protein Selectively Inhibits HIV Replication and Syncytium Formation", 1988, *Nature*, 331:78–81.
Kitamura et al., "A B Cell–Deficient Mouse by Targeted Disruption of the Membrane Exon of the Immunoglobulin µ Chain Gene", 1991, *Nature*, 350:423–26.
Kobayashi et al., "Reversal of Drug Sensitivity in Multidrug–Resistant Tumor Cells by an MDR1 (PGY1) Ribozyme", 1994, *Cancer Res.*, 54:1271–75.
Mahieu et al., "Construction of a Ribozyme Directed Against Human Interleukin–6 mRNA: Evaluation of Its Catalytic Activity In Vitro and In Vivo", 1994, *Blood*, 84:3758–65.
Mazzucco et al., "A Member of the Hsp70 Family of Heat–Shock Proteins is a Putative Target for the Immunosuppressant 15–Deoxyspergualin", 1993, *Ann. N.Y. Acad. Sci.*, 685:202–204.
Nadler et al., "Interaction of the Immunosuppressant Deoxyspergualin with a Member of the Hsp70 Family of Heat Shock Proteins", 1992, *Science*, 258:484–86.
Nadler et al., "Studies on the Interaction of the Immunosuppressant 15–Deoxyspergualin with Heat Shock Proteins", 1993, *Ann. N.Y. Acad. Sci.*, 696:412–414.
Roder et al., "The Beige Mutation in the Mouse Selectively Impairs Natural Killer Cell Function", 1979, *Nature*, 278:451–53.
Russell et al., "Identification and Upregulation of Galactose/N–acetylgalactosamine Macrophage Lectin in Rat Cardiac Allografts with Arteriosclerosis", 1994, *J. Clin. Invest.*, 94:722–30.
Russell et al., "Early and Persistent Induction of Monocyte Chemoattractant Protein 1 in Rat Cardiac Allografts", 1993, *Proc. Natl. Acad. Sci. USA*, 90:6086–90.
Shinkai et al., "RAG–2–Deficient Mice Lack Mature Lymphocytes Owing to Inability to Initiate V(D)J Rearrangement", 1992, *Cell*, 68:855–67.

(List continued on next page.)

Primary Examiner—Jasemine C. Chambers
Assistant Examiner—Karen M. Hauda
Attorney, Agent, or Firm—Fish & Richardson P.C.

[57] ABSTRACT

A mouse model for transplant arteriosclerosis useful for identifying compounds which reduce or prevent such arteriosclerosis, consisting of a mouse engrafted with a histoincompatible artery which exhibits detectable arteriosclerosis within 30 days of transplantation. Also disclosed are therapeutic methods for inhibiting the development of transplant arteriosclerosis in mammalian recipients of allografted organs.

32 Claims, 16 Drawing Sheets

OTHER PUBLICATIONS

Smith et al., "Blocking of HIV-1 Infectivity by a Soluble, Secreted Form of the CD4 Antigen", 1987, *Science*, 238:1704–1707.

Sterbenz et al., "Effects of 15–Deoxyspergualin on the Expression of Surface Immunoglobulin in 70Z/3.12 Murine Pre–B Cell Line", 1993, *Ann. N.Y. Acad. Sci.*, 685:205–206.

Sullivan, "Development of Ribozymes for Gene Therapy", 1994, *J. Invest. Derm.*, 103:85S–89S.

Tepper, "Deoxyspergualin: Mechanism of Action Studies of a Novel Immunosuppressive Drug", 1993, *Ann. N.Y. Acad. Sci.* 696:123–132.

Tepper et al., "15–Deoxyspergualin, a Novel Immunosuppressive Drug: Studies of the Mechanism of Action", 1993, *Ann. N.Y. Acad. Sci.*, 685:136–47.

Traunecker et al., "Soluble CD4 Molecules Neutralize Human Immunodeficiency Virus Type 1", 1988, *Nature*, 331:84–86.

Wang et al., "Human Recombinant Macrophage Inflammatory Protein–1α and –β and Monocyte Chemotactic and Activating Factor Utilize Common and Unique Receptors on Human Monocytes", 1993, *J. Immunology*, 150:3022–29.

Wiktor–Jedrzejczak et al., "Total Absence of Colony–Stimulating Factor 1 in the Macrophage–Deficient Osteopetrotic (op/op) Mouse", 1990, *Proc. Natl. Acad. Sci. USA*, 87:4828–32.

Adams, D.H., et al., "Hypercholesterolemia Does Not Exacerbate Arterial Intimal Thickening in Chronically Rejecting Rat Cardiac Allografts", 1989, *Trans. Proc.*, 21(1):437–39.

Adams, D.H., et al., "Inhibition of Graft Arteriosclerosis by Modulation of the Inflammatory Response", 1993, *Trans. Proc.* 25(2):2092–94.

Adams, D.H., et al., "Chronic Rejection in Experimental Cardiac Transplantation: Studies in the Lewis–F344 Model", 1993, *Immunol. Rev.*, 134:5–19.

Ardehali, A., et al., "Experimental Cardiac Allograft Vasculopathy in Mice", 1993, *J. Heart and Lung Trans.*, 12(5):730–35.

Billingham, M.E., "Graft Coronary Disease: The Lesions and the Patients", 1989, *Trans. Proc.*, 21(4):3665–66.

Corry, R.J., et al., "Heart Transplantation in Congenic Strains of Mice", 1973, *Trans. Proc.*, 5(1):733–35.

Cramer, D.V., et al., "Cardiac Transplantation in the Rat", 1989, *Transplantation*, 47(3):414–19.

Fingerle, J., et al., "Pituitary Factors in Blood Plasma are Necessary for Smooth Muscle Cell Proliferation in Response to Injury In Vivo", 1992, *Arteriosclerosis and Thrombosis*, 12(12):1488–95.

Foegh, M., et al., "Inhibition of Coronary Artery Transplant Atherosclerosis in Rabbits with Angiopeptin, an Octapeptide", 1989, *Atherosclerosis*, 78:229–36.

Häyry, P., et al., "Somatostatin Analog Lanreotide Inhibits Myocyte Replication and Several Growth Factors in Allograft Arteriosclerosis", 1993, *The FASEB, J.*, 7:1055–60.

Isik, F., et al., "Transplant Arteriosclerosis in a Rat Aortic Model", 1992, *Am. J. Pathol.*, 141(5):1139–49.

Kosek, J.C., et al., "Heart Graft Arteriosclerosis", 1971, *Trans. Proc.*, 3(1):512–14.

Laden, M.K., et al., "Experimental Atherosclerosis in Rat and Rabbit Cardiac Allografts", 1972, *Arch. Path.*, 93(1):240–45.

Meiser, B.M., et al., "Simvastatin Decreases Accelerated Graft Vessel Disease After Heart Transplantation in an Animal Model", 1993, *Trans. Proc.*, 25(2):2077–79.

Meiser, B.M., et al., "Continuous Infusion of Angiopeptin Significantly Reduces Accelerated Graft Vessel Disease Induced by FK 506 in a Rat Heart Allograft Model", 1992, *Trans. Proc.*, 24(5):1671–72.

Mennander, A., et al., "Chronic Rejection in Rat Aortic Allografts: An Experimental Model for Transplant Arteriosclerosis", 1991, *Arteriosclerosis and Thrombosis*, 11(3):671–80.

Mennander, A., et al., "Chronic Rejection in the Rat Aortic Allograft: V. Mechanism of the Angiopeptin (BIM 23014C) Effect on the Generation of Allograft Arteriosclerosis", 1993, *Transplantation*, 55(1):124–28.

Paul, L.C., "Chronic Rejection of Organ Allografts: Magnitude of the Problem", 1993, *Trans. Proc.*, 25(2):2024–25.

Russell, P.S., et al., "Coronary Atherosclerosis in Transplanted Mouse Hearts: I. Time Course and Immunogenetic and Immunopathological Considerations", 1994, 144(2):260–74.

Russell, P.S., et al., "Coronary Atherosclerosis in Transplanted Mouse Hearts: II. Importance of Humoral Immunity", 1994, *J. Immunol.*, pp. 5137–41.

Schmitz–Rixen, T., et al., "Immunosuppressive Treatment of Aortic Allografts", 1988, *J. Vasc. Surg.*, 7(1):82–92.

Effect of MHC-I Gene Deletion (30 days)

MHC-I Deletion    C57BL Control

Effect of MHC-II Gene Deletion (30 days)

MHC-II Deletion  C57BL Control

Effect of IgM CH$_4$ Deletion (30 days)

IgMCH$_4$ Deletion      C57Bl×129 Control

Effect of Absent Natural Killer Cells (30 days)

Bg Mice

C57BL Control

CELLULAR BASIS OF TRANSPLANT ARTERIOSCLEROSIS IN MICE

This application is a continuation-in-part of U.S. Ser. No. 08/277,489, now abandoned filed Jul. 18, 1994.

BACKGROUND OF THE INVENTION

The invention relates to organ transplantation.

Transplant-associated arteriosclerosis is the major cause of cardiac allograft failure after the first postoperative year, (Billingham, *Transplant Proc.*, 1989, 21:3665–66, and Sharples et al., *Transplantation*, 1991, 52:244–52) and it appears to be a significant problem in the long-term survival of other solid organ transplants (Paul, *Transplant. Proc.*, 1993, 25:2024–25, and Häyry et al., *Clin. Investigator*, 1992, 70:780–90.). Also, despite the success of immunosuppressive agents in the treatment of acute rejection, there is considerable debate about whether these drugs influence the progression of transplant arteriosclerosis in animal models (Arai et al., *J. Heart Lung Transplant*, 1992, 11:757–62, Cramer et al., *Transplantation*, 1990, 50:554–58, Meiser et al., *Lancet*, 1991, 338:1297–98, and Mennander et al., *Transpl. Int.*, 1991, 4:173–79). Both the gross and the histologic features of transplant arteriosclerosis differentiate it from commonly occurring (chronic) arteriosclerosis. In contrast with common arteriosclerosis, the lesion associated with transplant arteriosclerosis involves the artery in a concentric rather than eccentric fashion and often involves both the epicardial coronary arteries and the intramyocardial branches (Billingham, 1989, supra). Lipid accumulation is less common in the early development of the transplant-associated lesion (Pucci et al., *J. Heart Transplant*, 1990, 9:339–45), and the development of the disease is faster (Sharples et al., 1991, supra). Although the complexity of the transplant-associated lesion and the many cell types involved, as well as the participation of a variety of growth factors and cytokines, suggest stimulation by an immune mechanism, such as delayed type hypersensitivity (Schoen et al., *Trends Cardiovasc. Med.*, 1991, 1:216–23), the immunological mechanisms which contribute to the pathogenesis of the disease have not been defined.

SUMMARY OF THE INVENTION

The invention features a mouse model of transplant arteriosclerosis, and a method useful for evaluating strategies to prevent or treat the development of transplantation arteriosclerosis. In addition to the use of the model in evaluating the efficacy of candidate compounds or other therapeutic interventions, the etiology of the disease may be determined in accordance with the invention using strains of mice which harbor specific gene deletions.

The invention provides a surgically modified mouse in which a histoincompatible artery which is not part of a solid organ, or which has been removed from a solid organ, has been transplanted into, i.e., spliced into, an endogenous artery. The transplanted histoincompatible artery in the mouse of the invention exhibits transplant arteriosclerosis within 30 days of transplantation.

In another embodiment of the invention, the mouse may be engrafted with both an artery from a histoincompatible mouse and (as a control) an artery from a histocompatible mouse. The arteriosclerotic lesion which develops in a transplanted histoincompatible artery is at least 100% greater than that which develops in a transplanted histocompatible artery.

Both the transplanted and endogenous arteries may be carotid arteries. Alternatively, the endogenous artery may be a carotid artery and the transplanted artery may be any other type of artery, e.g., a femural artery or an aortic artery.

"Histoincompatible", as used herein, refers to the relationship between (1) the recipient of a transplanted tissue or graft, e.g., the transplanted artery, and (2) the donor of the transplanted tissue, and is defined as disparity between (a) the recipient's cell surface antigens (or genes encoding such antigens) which mediate immunologic rejection of a transplanted tissue, and (b) those of the donor. One major locus of genes, the major histocompatibility complex (MHC), determines the fate of a graft, i.e., whether the graft will survive or be rejected; other loci (minor histocompatibility loci) also contribute to graft rejection. The histoincompatible transplanted artery may differ from the recipient at one or more MHC loci, one or more minor histoincompatibility loci, or both.

The murine histocompatibility complex is referred to as the H-2 complex. Mice of the same inbred strain may be isogenic (identical with respect to all their genes) or syngeneic (identical with respect to genes which govern immunologic graft rejection); mice of different inbred strains are allogeneic (different with respect to genes which govern graft rejection).

The mouse of the invention (host or recipient mouse) may be of a different haplotype than the murine donor of the tranplanted artery. The host and donor mice may be of any haplotype provided that they are histoincompatible. Preferably the mouse of the invention has an $H-2^b$ haplotype and the murine donor of the transplant artery has an $H-2^{h2}$ haplotype, e.g., the host mouse is of the C57BL/6J strain and the murine donor is of the B.10A(2R) strain. Alternatively, the mouse of the invention has an $H-2^{h2}$ haplotype and the murine donor has an $H-2^b$ haplotype. "Haplotype", as used herein, refers to a stably linked cluster of genes of the H-2 locus. Each inbred strain has a characteristic haplotype, e.g., $H-2^b$, $H-2^d$, $H-2^k$, $H-2^a$, $H-2^{h2}$. Some different inbred strains have the same haplotype, e.g., the inbred strains C57BL/10, C67BL/6 and BALB.b all have the $H-2^b$ haplotype. Strains with the same haplotype may differ at genetic loci outside the major histocompatibility complex, i.e., minor histocompatibility loci.

The mouse of the invention may be made using mouse strains harboring one or more gene deletions, e.g., Rag-2 gene deletion (absence of rearrangement in both T cell receptors and antibodies and thus no antigen-specific immune response); MHC II gene deletion (absence of $CD4^+$ T cells); MHC I gene ($\beta_2$ microglobulin) deletion (absence of $CD8^+$ T cells); gene deletion of the transmembrane domain of the μ chain of IgM (absence of specific humoral antibodies and B cells); OP/OP homozygous mice (a spontaneous mutant strain in which macrophage colony stimulation factor (MCSF) is absent with consequent marked reduction in macrophage production); and Beige (Bg) mice (a spontaneous mutant strain in which natural killer cell function is deficient).

The invention also provides an in vivo screening assay to determine whether a compound reduces transplant arteriosclerosis, by providing a first mouse of a first inbred strain, which mouse contains a first artery transplanted from a histoincompatible donor mouse, i.e., an allograft, and a second mouse of the first inbred strain, which second mouse contains a second artery transplanted from a histoincompatible donor mouse of the second inbred strain; contacting the first artery with a candidate compound; and comparing the degree of arteriosclerosis in each graft within 30 days after transplantation. The candidate compound is preferably a compound which inhibits macrophage activity, B cell activity, or CD4⁺ T cell activity, either directly or indirectly. Arteriosclerosis can be detected in the transplanted artery as early as 7 days after transplantation. The transplanted artery may be removed from the mouse at any point during the assay and preserved, e.g., frozen for subsequent analysis. The candidate compound may be administered locally so as to contact the first artery directly; alternatively, the compound may be delivered systemically so the artery is contacted with compound via the circulatory system. A lesser degree of arteriosclerosis in the first histoincompatible artery compared to the second histocompatible artery is an indication that the candidate compound reduces transplant arteriosclerosis. As a control, an artery from a histocompatible donor mouse, i.e., a syngraft or isograft, can be transplanted into each test mouse, in addition to the allografted artery. Another mouse of the first inbred strain containing an isograft or a syngraft may also be used as a control. In the absence of treatment, transplant arteriosclerosis in the test mouse, i.e., in the allografted artery, is at least 100% greater than that in the control mouse, i.e., in the isografted artery.

Degree of transplant arteriosclerosis may be determined by physically measuring neointimal thickening, or by characterizing and enumerating cells involved in the rejection process, e.g., smooth muscle cells, leukocytes, macrophages, and subpopulations of lymphocytes (CD4⁺ and CD8⁺ cells). The intima is defined as the region between the lumen and the internal elastic lamina of the artery; the media is defined as the region between the internal and external elastic laminae; and the adventitia is defined as the region outside the external elastic lamina of the artery. Functional activity, e.g., production of cytokines, of the infiltrating cells can also be measured to determine the degree of transplant arteriosclerosis. Replicating cells which contribute to the formation of the arteriosclerotic lesion may be detected by expression of proliferating cell nuclear antigen (PCNA).

Any arteries may be used in the screening assay of the invention. For example, the grafted arteries may both be carotid arteries or aortic arteries. Alternatively, the donor artery or recipient artery, or both, may be in a solid organ, e.g. a heart, liver or kidney. Preferably, the endogenous artery and the engrafted artery are carotid arteries. The first and second inbred strains are preferably of different haplotypes; for example, the host mouse may have an H-2$^b$ haplotype (C57BL/6J) and the donor mouse an H-2$^{k2}$ haplotype (B.10A(2R)).

The invention also includes a method of making the surgically modified mouse of the invention. The method can be carried out as follows: a first mouse of a first inbred strain is provided; an artery which is not part of a solid organ, or which has been removed from a solid organ ("the transplant artery") is surgically removed from a second mouse of a second inbred strain; and the transplanted artery is surgically attached (spliced) to an endogenous artery of the first mouse, such that the functional integrity of the blood vessel is restored, i.e., pulsation of the vessel and blood flow through the artery is evident.

One major advantage of the inventive model is that the development of transplant arteriosclerosis in this model closely parallels the development of the disease in humans. Like the human disease, staged development of lesions with mixed cellular characteristics involving both inflammatory cell and smooth muscle cell accumulation occurs in the mouse of the invention. Another important feature of the model is a high degree of reproducibility at each time point of arteriosclerotic development.

A second advantage is the accelerated pace at which arteriosclerotic lesions develop. A neointima begins to develop in allografts as early as 7 days after grafting, and it becomes a nearly occlusive lesion after 30 days. The pace of development of transplant arteriosclerosis in the mouse of the invention allows the evaluation of drugs or other types of therapeutic intervention in 30 days or less. In contrast, arteriosclerotic lesions in other animal models, e.g., the rat, are significantly slower to develop and not as florid as those in the mouse.

Another significant advantage of the invention is that intimal proliferation is minimal in mouse isografts, permitting a sharp contrast with the results in allografted arteries. Isografted arteries either did not develop a neointima, or developed a neointima of only one cell layer in thickness on a small portion of the luminal circumference. The neointima seen in allografts, but not in isografts, appears to be the product of an immunologically mediated reaction rather than of surgical trauma or ischemia.

In contrast, a major disadvantage of the rat model which has been used to study cardiac transplantation is that significant lesions develop in control (syngeneic) transplants (Pucci et al., *J. Heart Transplant*, 1990, 9:339–345; Adams et al., *Transplant Proc.* 1989, 21:437–439; Adams et al., *Immunol. Rev.* 1993, 134:5–19; Mennander et al., *Transplantation*, 1993, 55:124–128).

Another advantage of the invention is that syngeneic and allogeneic grafts can be compared in the same animal.

Also, the murine carotid artery graft procedure, which is carried out subcutaneously in the neck, is not as technically complex as the procedure used in some other models, e.g., abdominal cardiac transplantation (Corry et al., *Transplant Proc.*, 1973, 5:733–35), which requires invasion of the peritoneal space with attendant potential complications. As a result, transplantation success rate is relatively high in the mice of the invention with carotid artery grafts. Because the common carotid artery is unbranched from its origin in the aorta to its bifurcation, quantitation and morphometric studies are simplified.

Yet another advantage of the inventive model is that transplantation of an artery in the absence of a solid organ allows the study of vascular rejection in the absence of surrounding parenchyma.

The inventive mouse model of transplant arteriosclerosis has been used to elucidate the immune mechanisms which contribute to the development of transplant arteriosclerosis. Accordingly, the invention features a method of inhibiting transplant arteriosclerosis in a mammalian recipient (e.g., a human patient) of an allografted organ, by administering to the recipient a therapeutic composition which inhibits the activity of CD4-positive T cells but not CD8-positive T cells (cytotoxic T cells), inhibits an humoral immune response, and/or inhibits macrophage activity. By "CD4-positive T cell activity" is meant proliferation, cytokine production, and/or helper function in stimulating antibody production or isotype switching in B cells by T cells. By "CD8-positive T cell activity" is meant the ability of CD8⁺ T cells to kill target cells, i.e., cytotoxicity. By "macrophage activity" is meant proliferation, migration to a graft site, cytokine production and/or antigen presentation by macrophages. Compounds which inhibit macrophage activity may also be administered to the donor organ ex vivo prior to transplantation into the mammalian recipient.

In another aspect, the invention includes a method of inhibiting transplant arteriosclerosis in a recipient mammal by administering to the recipient a compound which inhibits a humoral immune response. An immunosuppressive compound, e.g., 15-deoxyspergualin, may be administered to the recipient to suppress the activity of B cells. By "B cell activity" is meant proliferation, antigen presentation and/or immunoglobulin production by B cells. Any B cell immunosuppressive agent can be tested for the ability to inhibit transplant arteriosclerosis using the claimed screening methods; a compound found to have inhibitory activity in the mouse model of transplant arteriosclerosis can then be used in the therapeutic methods of the invention.

The invention also includes a method of inhibiting transplant arteriosclerosis in a mammalian recipient of an allografted organ by administering to the recipient a compound which inhibits macrophage activity. Alternatively, the method may be carried out by contacting a donor organ either in vivo or ex vivo with a compound which inhibits macrophage activity, and if the contacting step was carried out ex vivo, then transplanting the organ into the recipient mammal. Preferably, the compound inhibits expression or activity of macrophage colony stimulating factor or galactose/N-acetylgalactosamine macrophage lectin. The compound may also inhibit expression of the oligosaccharide, galactose/N-acetylgalactosamine (which binds to galactose/N-acetylgalactosamine macrophage lectin), in the donor organ. Antibodies which bind to either the macrophage lectin or its oligosaccharide ligand may be used to block binding of lectin to its oligosaccharide ligand, thereby inhibiting macrophage activity at the graft site. The compound may inhibit macrophage colonization of the donor organ, for example, by inhibiting expression or activity of a macrophage or monocyte chemoattractant protein. An antibody which binds to a macrophage or monocyte chemoattractant protein may also be used to inhibit macrophage colonization of the engrafted organ. For example, antibodies which bind to chemoattractant factors such as monocyte chemoattractant protein-1, macrophage inflammatory protein-1α, or macrophage inflammatory protein-1β, may be administered to the recipient to inhibit macrophage migration to the graft site.

In a final aspect, the invention includes a method of inhibiting transplant arteriosclerosis in a mammalian recipient of an allografted organ by administering to the recipient a compound which inhibits the activity of CD4-positive T cells but not CD8-positive T cells, e.g., soluble CD4 or a CD4-immunoglobulin fusion protein. The method may also be carried out by contacting a donor organ either in vivo or ex vivo with a compound which inhibits proliferation of CD4-positive T cells but not CD8-positive T cells, and if the contacting step was carried out ex vivo, then transplanting the organ into the recipient mammal. For example, an organ may be contacted with a compound which inhibits the expression of a Class II MHC antigen on the surface of an antigen presenting cell, thereby preventing the binding of $CD4^+$ T cells to cells of the donor organ (and thus $CD4^+$ T cell activation). Other compounds which selectively inhibit the activity of $CD4^+$ T cells (and inhibit transplant arteriosclerosis as measured by the screening assays of the invention) may also be used to treat transplant arteriosclerosis according to the invention.

Other features and advantages of the invention will be apparent from the following description of the invention and from the claims.

DETAILED DESCRIPTION

The drawings will first be briefly described. The file of this patent contains at least one drawing executed in color. Copies of this patent with color drawings will be provided by the PTO upon request and payment of the necessary fee.

Drawings FIG. 1 is a photograph of an operative field showing the left recipient carotid artery to which the donor artery loop has been sutured.

The elastic lamina are shown stained in black in each of FIGS. 2A–2E. All sections shown in FIGS. 2A–2E were embedded in paraffin and viewed at final magnification of 850×.

Figure 3A:
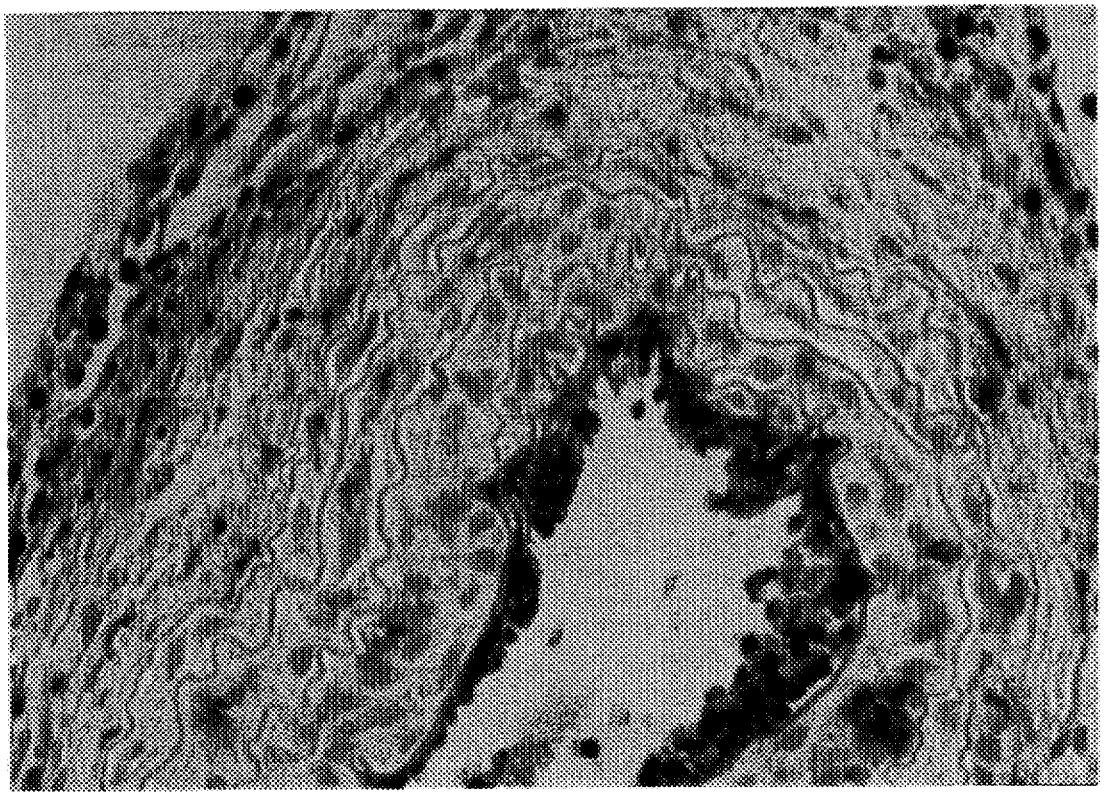

FIG. 3A is a photograph of a microscopic cross section of an allografted artery (7 days post-transplantation) stained for the leukocyte marker, CD45 (brown).

Figure 3B:
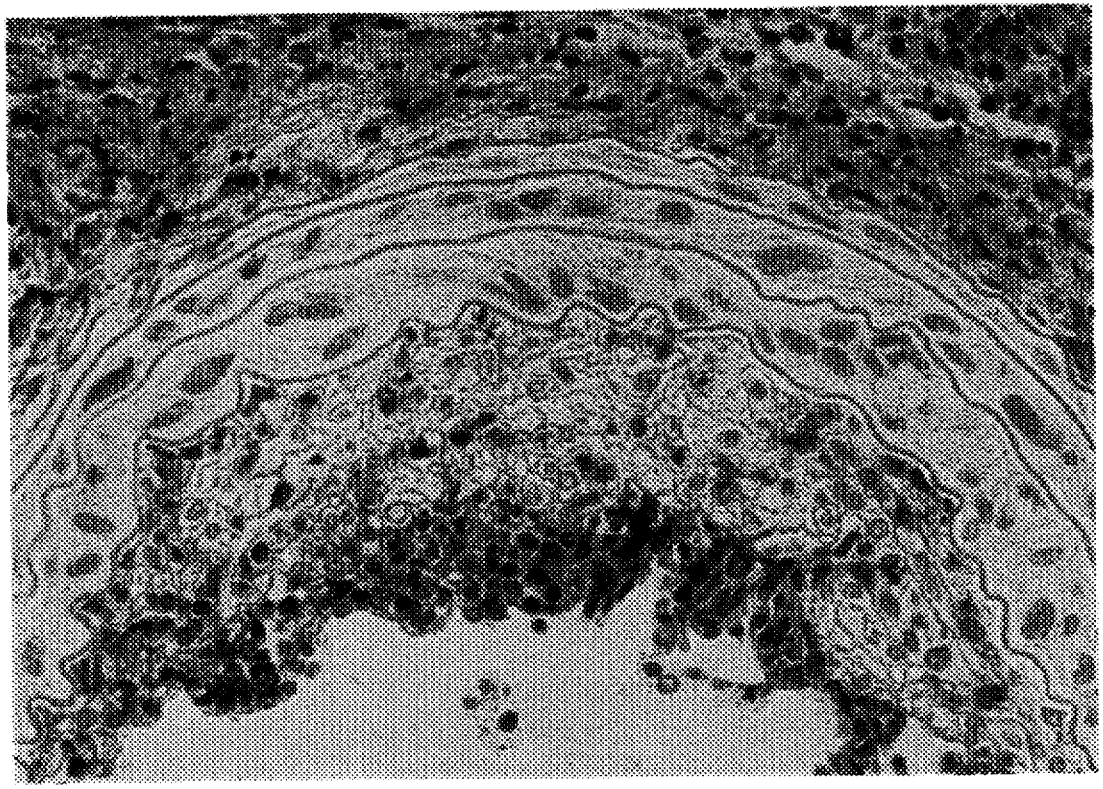

FIG. 3B is a photograph of a microscopic cross section of an allografted artery (15 days post-transplantation) stained for the leukocyte marker, CD45 (brown).

Figure 3C:
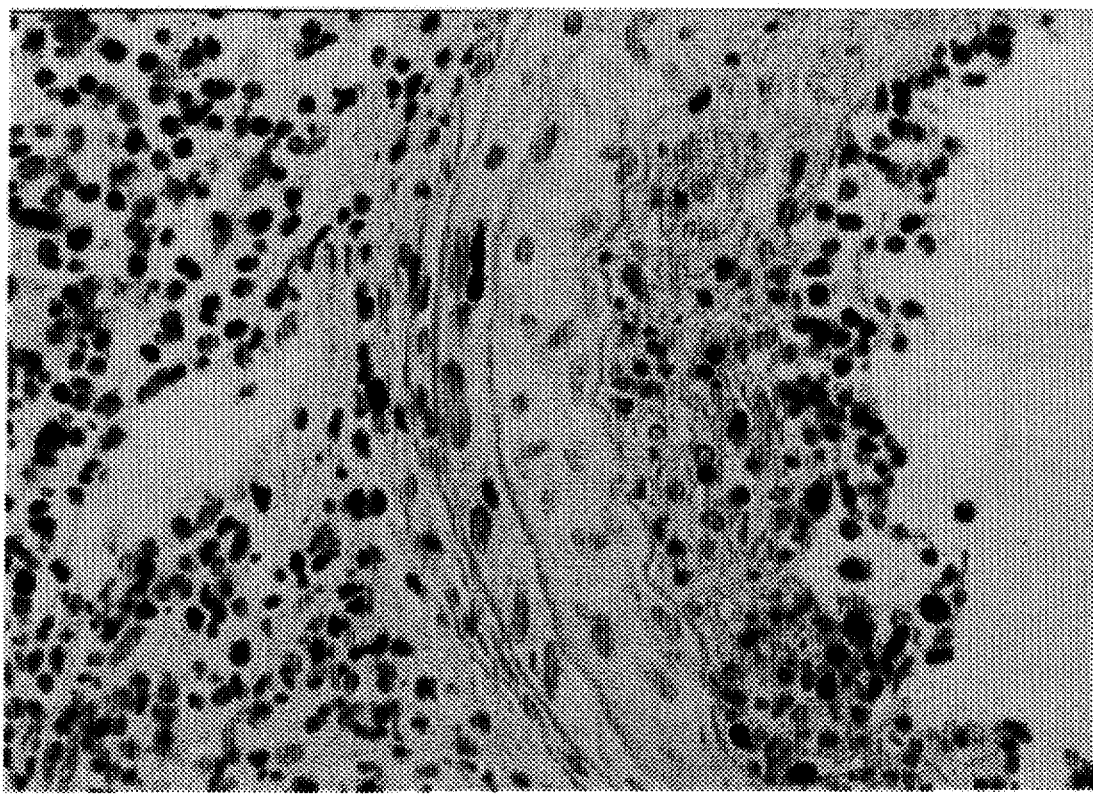

FIG. 3C is a photograph of a microscopic cross section of an allografted artery (15 days post-transplantation) stained for PCNA (dark brown).

Figure 3D:
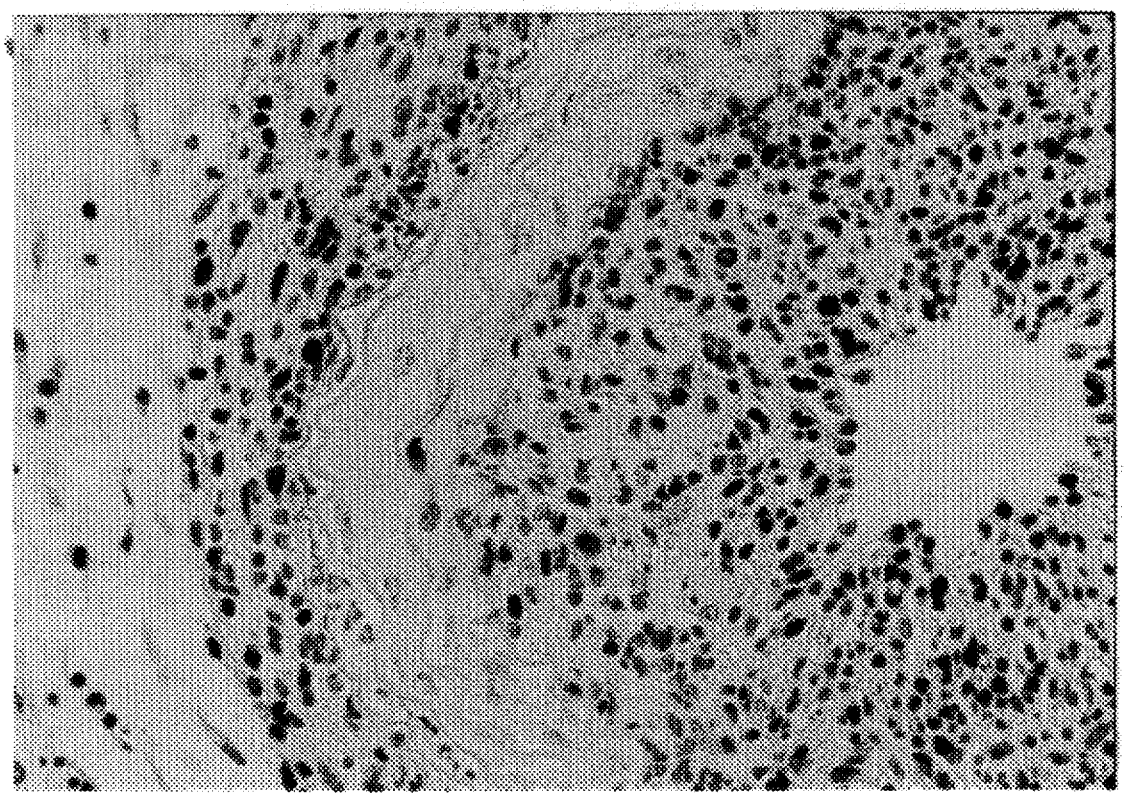

FIG. 3D is a photograph of a microscopic cross section of an allografted artery (30 days post-transplantation) stained for PCNA (dark brown).

Figure 3E:
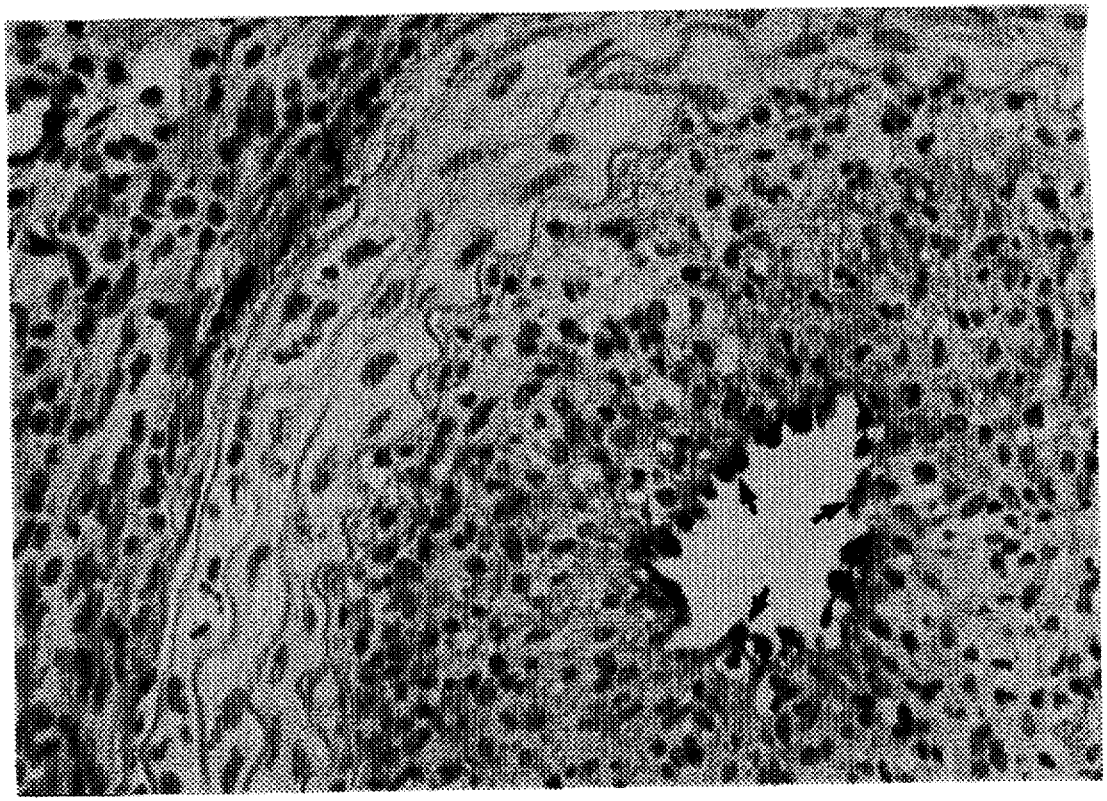

FIG. 3E is a photograph of a microscopic cross section of an allografted artery (30 days post-transplantation) stained for von Willebrand factor (dark brown, arrows).

Figure 3F:
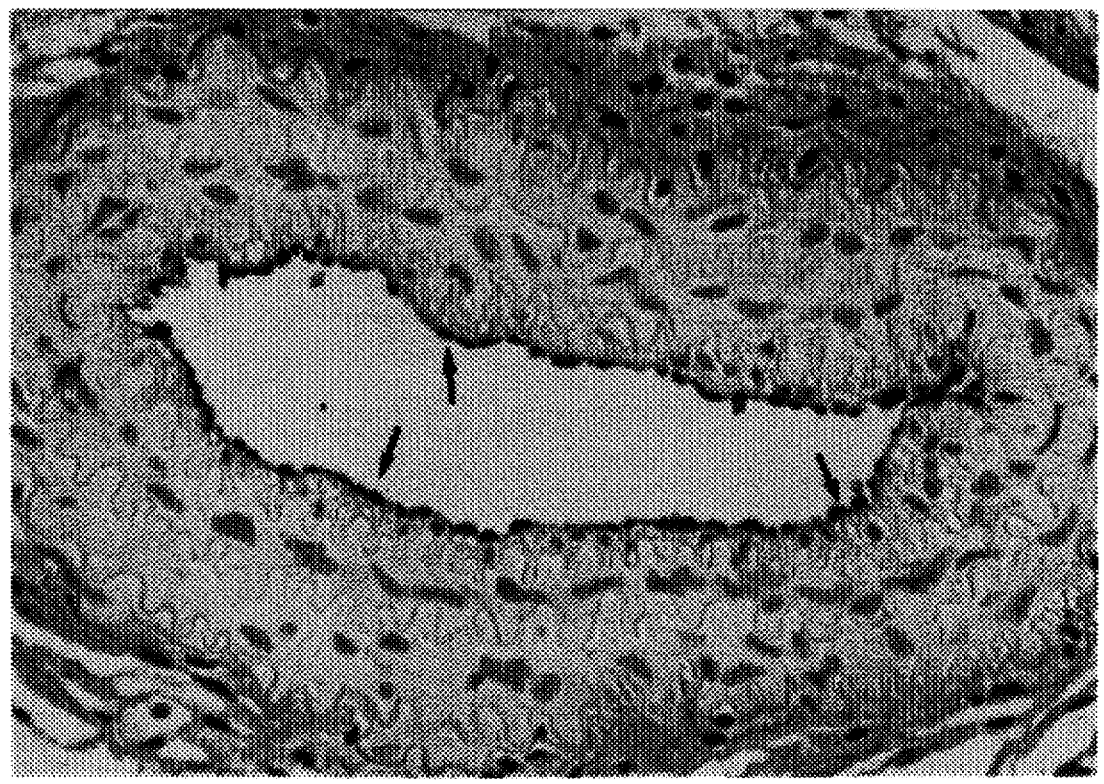

FIG. 3F is a photograph of a microscopic cross section of an isografted artery (30 days post-transplantation) stained for von Willebrand factor (dark brown, arrows).

All sections shown in FIGS. 3A–3F were counterstained with methyl green, embedded in paraffin, and viewed at a final magnification of 850×.

Figure 4A:
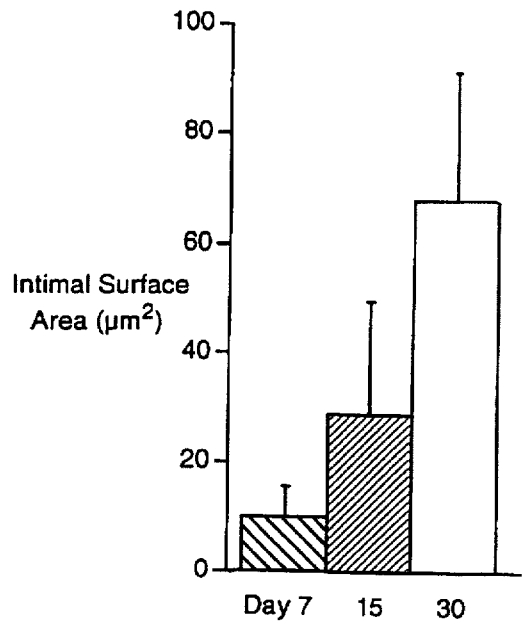

FIG. 4A is a bar graph showing a comparison of intimal cross-sectional area (7, 15, and 30 days post-transplantation). The area observed on day 30 was greater than that observed on day 15 ($P=0.0002$); the area observed on day 30 was greater than that observed on day 7 ($P<0.0005$).

Figure 4B:
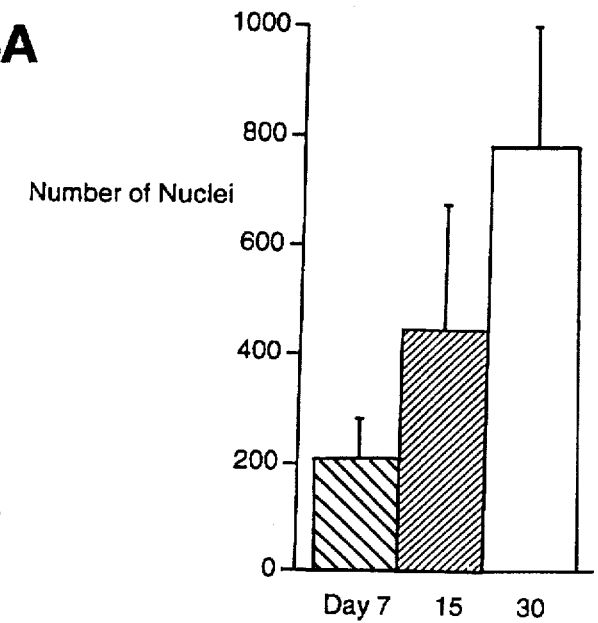

FIG. 4B is a bar graph showing a comparison of nuclei detected in an intimal cross-sectional area (7, 15, and 30 days post-transplantation). The number of nuclei detected on day 15 was greater than that detected on day 7 ($P=0.025$); the number of nuclei detected on day 30 was greater than that detected on day 15 ($P=0.001$).

Figure 4C:
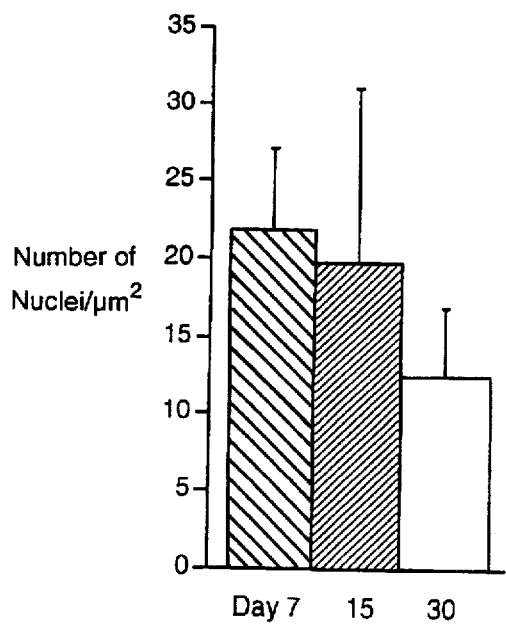

FIG. 4C is a bar graph showing a comparison of intimal cell density (7, 15, and 30 days post-transplantation). The density measured on day 30 was greater than that measured on day 7 ($P=0.02$).

Intimal cell parameters plotted in FIGS. 4A–4C are expressed as mean ±SD. At least seven cross-sections were measured for each data point.

Figure 5A:
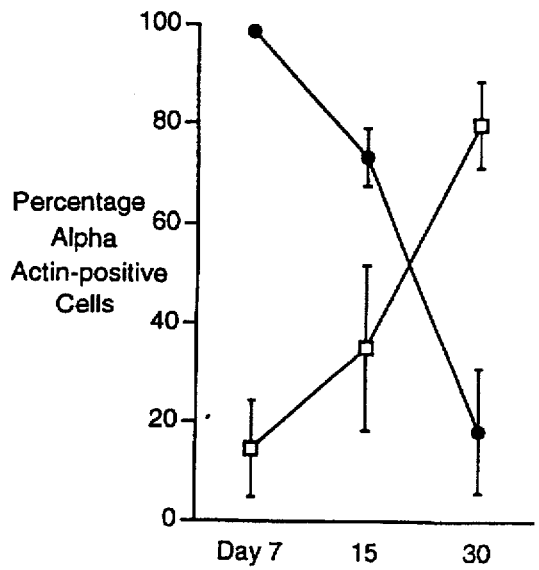

FIG. 5A is a line graph showing a immunocytochemical quantification of alpha actin-positive intimal [□] and medial

[•] cells (7, 15, and days 30 post-transplantation). The number of neointimal alpha actin-positive cells increased significantly between day 7 and day 30 (P<0.0006), while the number of medial alpha actin-positive cells decreased (P<0.00005).

Figure 5B:
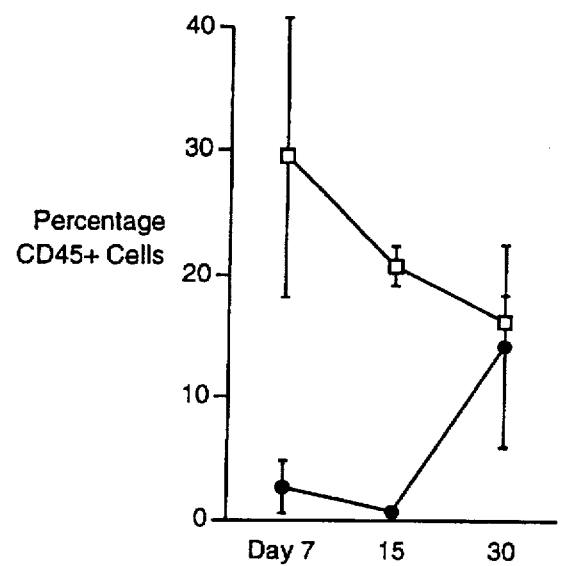

FIG. 5B is a line graph showing a immunocytochemical quantification of $CD45^+$ intimal [□] and medial [•] cells (7, 15, and 30 days post-transplantation). The number of neointimal $CD45^+$ cells decreased between day 7 and day 30 (P=0.05), and the number of medial $CD45^+$ cells increased (P=0.03).

Figure 5C:
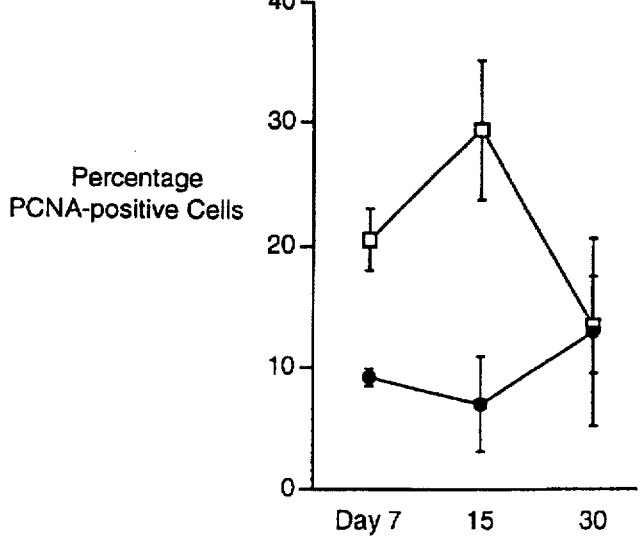

FIG. 5C is a line graph showing a immunocytochemical quantification of PCNA-positive intimal [□] and medial [•] cells (7, 15, and 30 days post-transplantation). The number of neointimal PCNA-positive cells decreased between day 15 and day 30 (P=0.004). The percentage of cells staining for PCNA in the media, i.e., the region between the internal and external elastic laminae of the artery, did not change significantly with time.

Each data point graphed in FIGS. 5A–5C represents the mean from three samples ±SD.

Figure 6A:
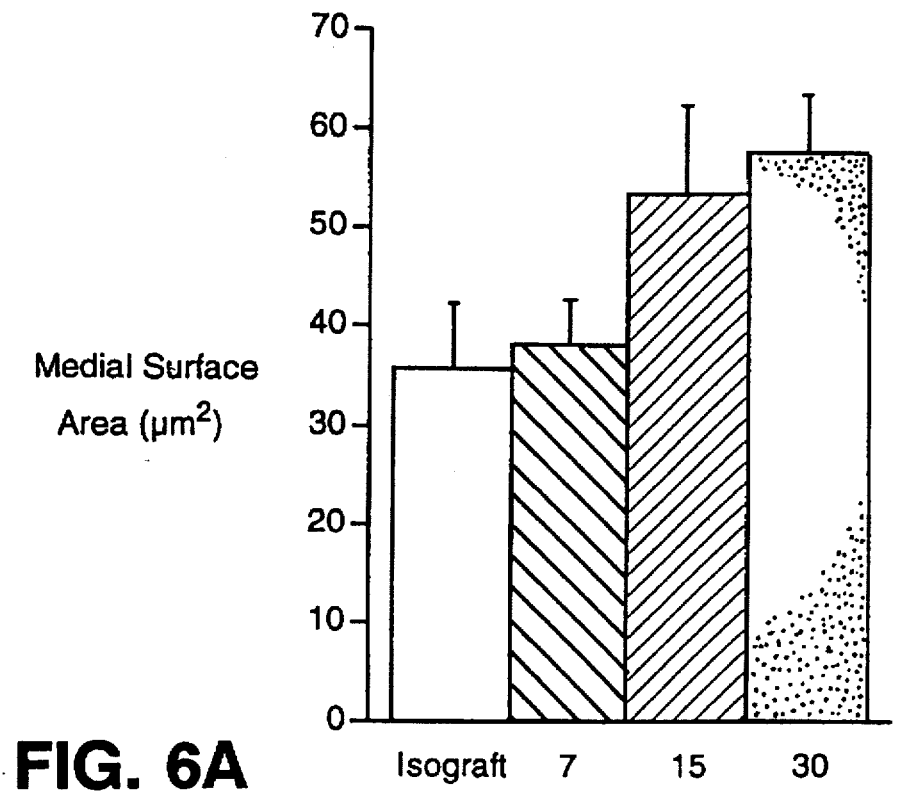

FIG. 6A is a bar graph showing a comparison of medial cross-sectional areas of tranplanted arteries. The area observed in an allografted artery on day 15 post-transplantation was greater than that observed on day 7 (P<0.0002).

Figure 6B:
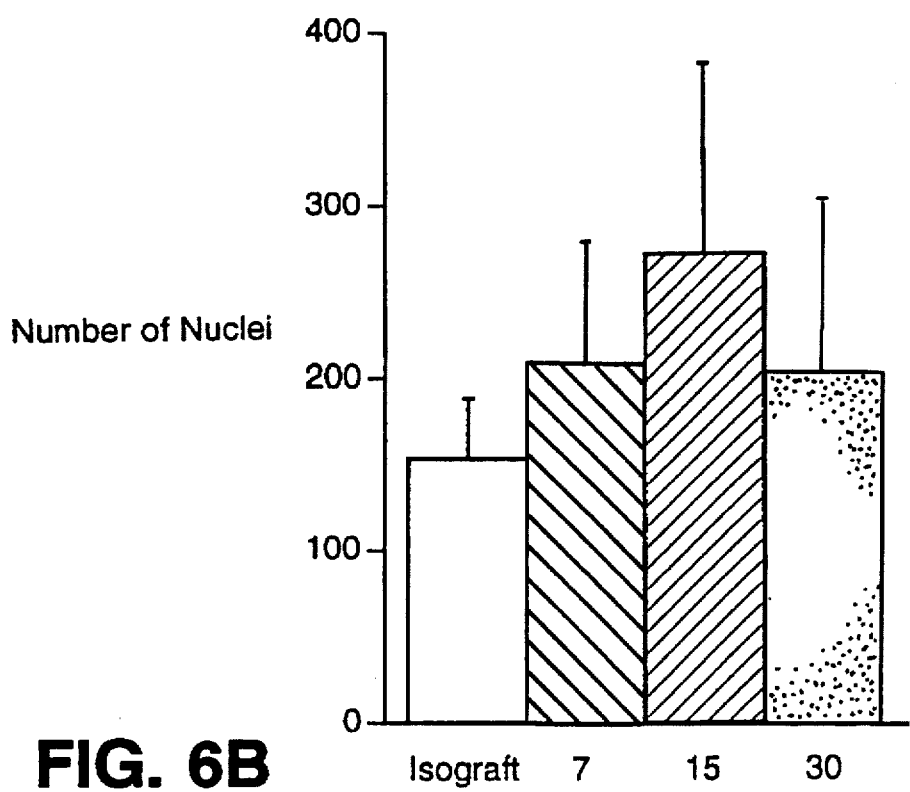

FIG. 6B is a bar graph showing a comparison of total medial nuclei in medial cross-sectional areas of transplanted arteries. No significant difference was observed among the time points.

Medial cell parameters graphed in FIGS. 6A–6B are expressed as mean ±SD. At least seven cross-sections were measured for each data point plotted in each of FIGS. 6A–6B.

Figure 7A:
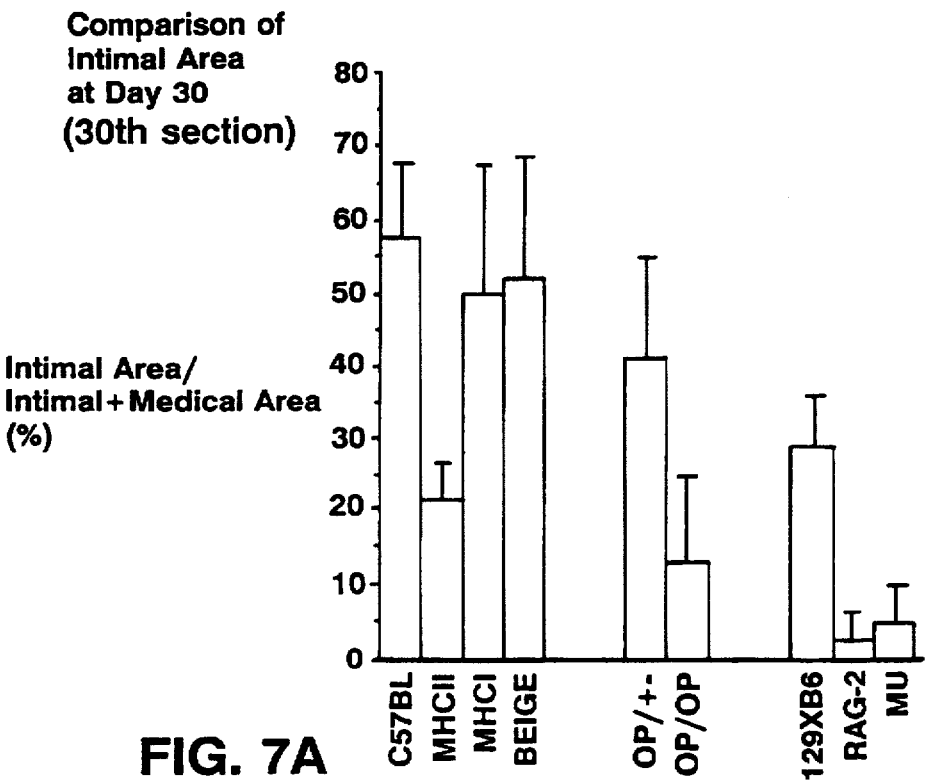

FIG. 7A is a bar graph showing a comparison of intimal areas (30th 5 micron histological section from the center of the transplanted carotid loop) at day 30 after transplantation into mouse strains with various gene deletions (indicated in the x-axis).

Figure 7B:
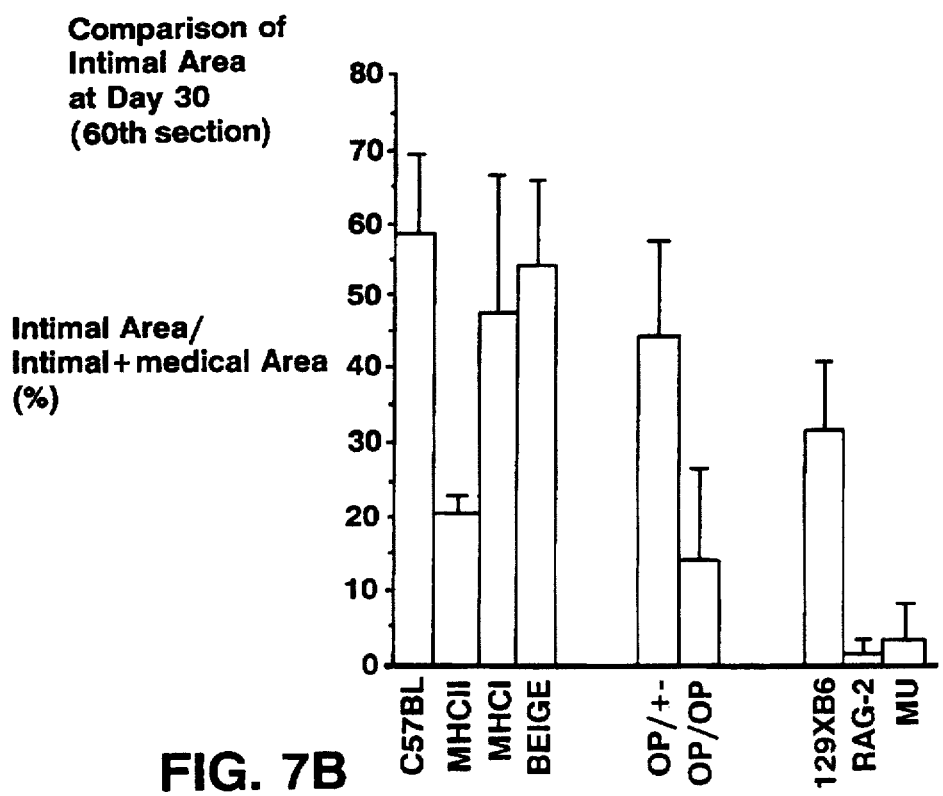

FIG. 7B is a bar graph showing a comparison of intimal areas (60th 5 micron histological section from the center of the transplanted carotid loop) at day 30 after transplantation into mouse strains with various gene deletions (indicated in the x-axis).

Figure 8:
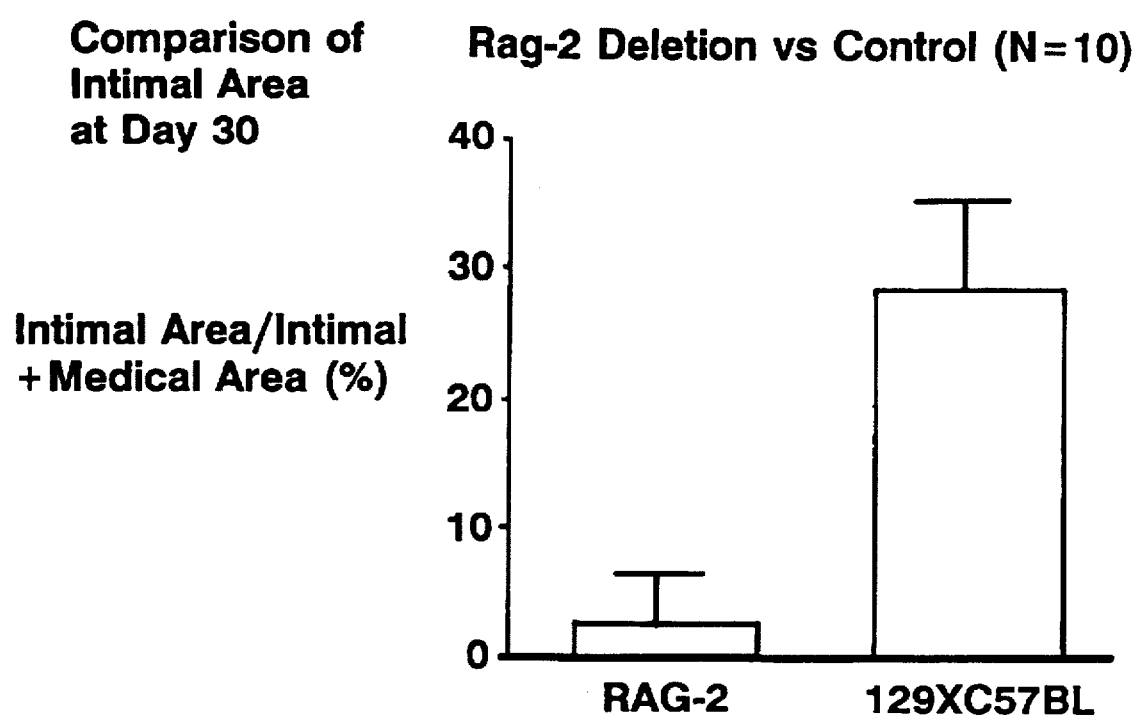

FIG. 8 is a bar graph showing intimal areas at day 30 after transplantation into the Rag-2 mouse strain compared to a control mouse strain.

Figure 9:
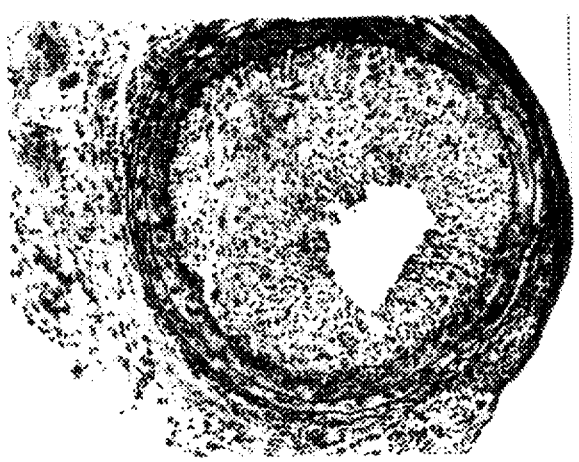
Figure 9:
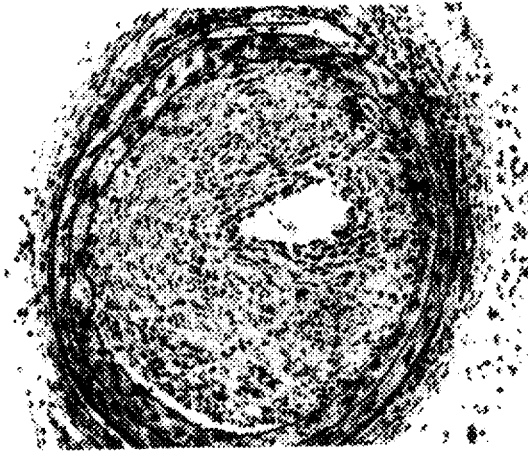

FIG. 9 is a photograph of a microscopic cross section of an allografted artery (30 days post-transplantation) into a mouse strain with a MHC Class I deletion compared to a similar section of an allografted artery transplanted into a control mouse strain.

Figure 10:
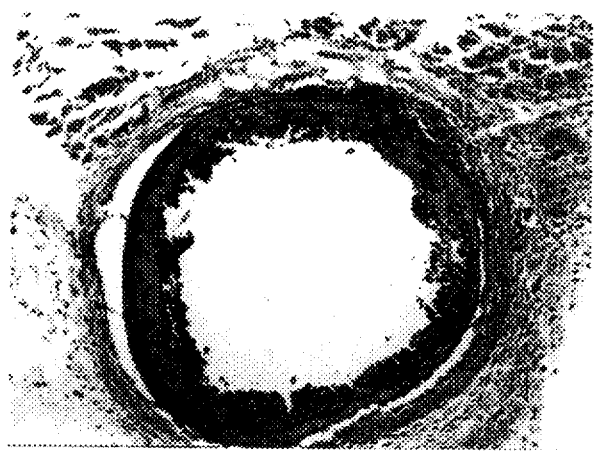
Figure 10:
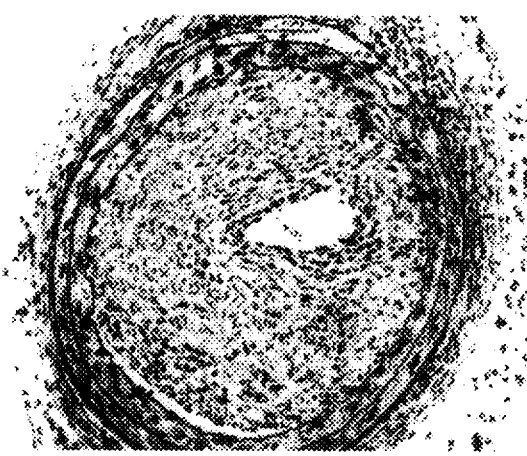

FIG. 10 is a photograph of a microscopic cross section of an allografted artery (30 days post-transplantation) into a mouse strain with a MHC Class II deletion compared to a similar cross section of an allografted artery transplanted into a control mouse strain.

Figure 11:
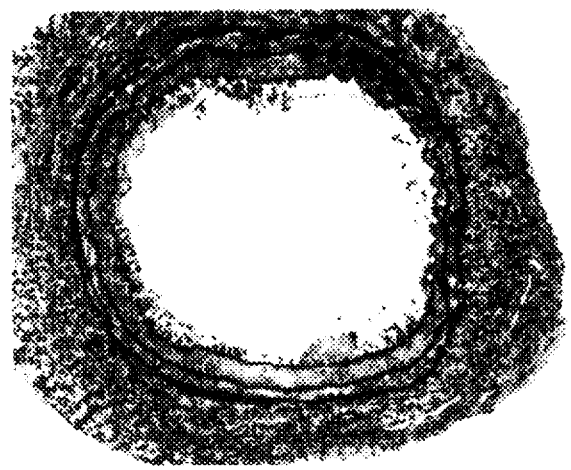
Figure 11:

FIG. 11 is a photograph of a microscopic cross section of an allografted artery (30 days post-transplantation) into a mouse strain with a IgM CH4 deletion compared to a similar cross section of an allografted artery transplanted into a control mouse strain.

Figure 12:
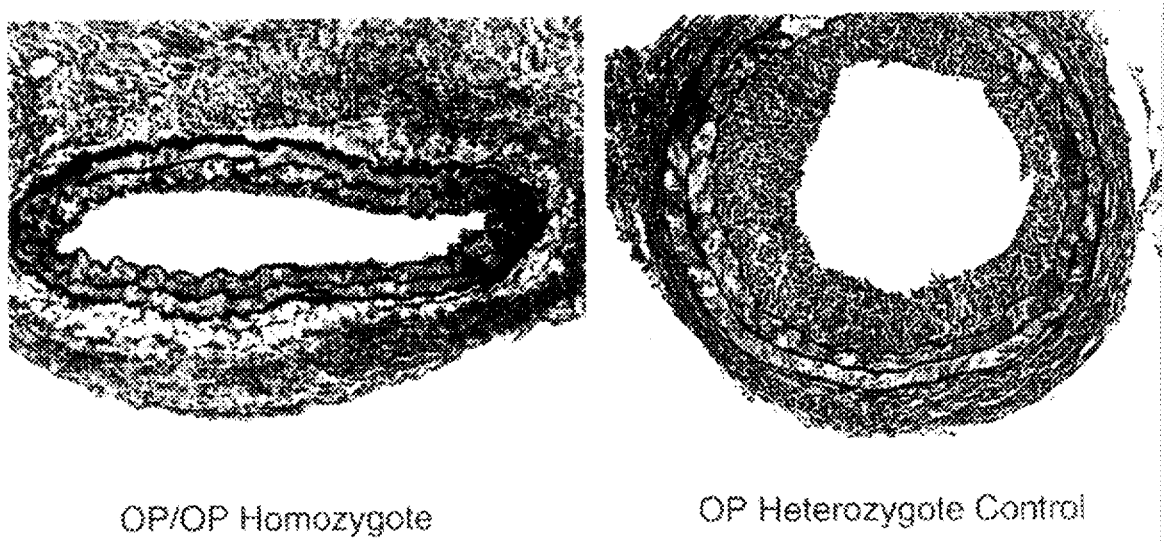

FIG. 12 is a photograph of a microscopic cross section of an allografted artery (30 days post-transplantation) into an OP/OP homozygote mouse strain compared to a similar cross section of an allografted artery transplanted into an OP heterozygote control mouse strain.

Figure 13:
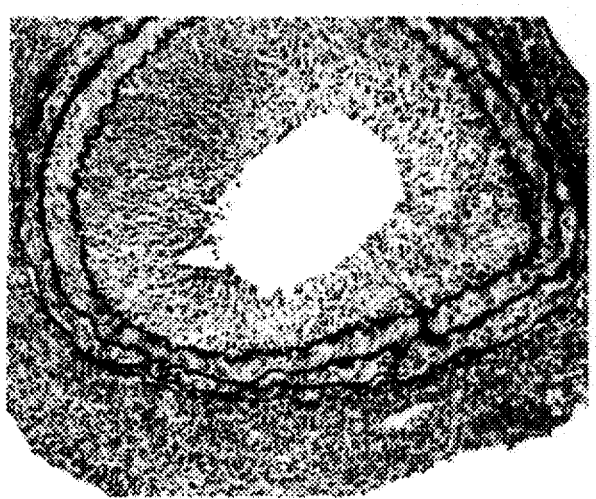
Figure 13:
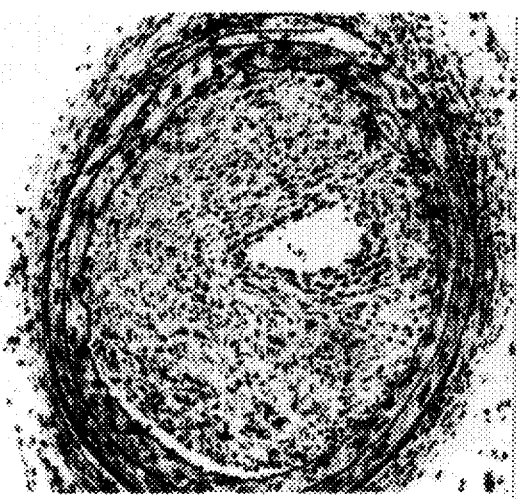

FIG. 13 is a photograph of a microscopic cross section of an allografted artery (30 days post-transplantation) into a Beige (Bg) mouse strain (lacking NK cells) compared to a similar cross section of an allografted artery transplanted into a control mouse strain.

In Vivo Model of Transplant Arteriosclerosis

The invention provides an accelerated model for transplant arteriosclerosis. The mouse of the invention, which reproduces many of the features of human transplant arteriosclerosis at an accelerated pace, can be used to test a variety of therapeutic interventions for the prevention or treatment of transplant arteriosclerosis, the major reason for graft failure and death in cardiac transplantation. The mouse can also be used to determine the roles of genes that encode components of immunologic and inflammatory responses in the development of arteriosclerotic lesions.

To evaluate transplant arteriosclerosis in mice, carotid arteries were transplanted between B.10A(2R) ($H-2^{h2}$) donor mice and C57BL/6J ($H-2^b$) recipients, and compared with arteries isografted between C57BL/6J ($H-2^b$) mice. Immunosuppressive drugs were not used. Within 7 days, the allografted carotid artery formed a neointima containing mononuclear leukocytes ($CD45^+$) that were predominantly monocytes or macrophages (i.e., $CD11^+$ cells with single-lobed nuclei). $CD4^+$ and $CD8^+$ cells were present as well. By 30 days, the neointima became exuberant, and mononuclear leukocytes were largely replaced by smooth muscle cells. Cells staining for PCNA were present in the intima at both early and late time points, indicating the proliferation of mononuclear leukocytes and smooth muscle cells. The area of the intima increased from day 7 to day 30, as did the number of nuclei, but the density of the nuclei decreased, suggesting the formation of extracellular matrix. In contrast, there are few changes in the isografted artery.

In addition to its use as a screening tool, the mouse of the invention also provides a powerful tool for dissecting the relative contributions that humoral antibodies, specific cytokines or growth factors, cytotoxic T cells, and macrophages make to the pathogenesis of the disease.

Relevance to Human Disease

In many respects, the morphologic features of this mouse vascular transplant model resemble those of human transplant arteriosclerosis. Like the human lesions, the arterial lesions in the mouse of the invention are characterized by concentric intimal proliferation, with a dominance of smooth muscle cells accompanied by macrophages and T cells in the late stages. Intimal thickening impinges on the lumen of the vessel in both the human and the mouse. Also, inflammatory cells infiltrate the adventitia in both species.

Although the loss of smooth muscle cells from the media has not been described in the human lesion, this difference between human lesions and murine lesions may be attributed to the use of immunosuppressive agents in clinical transplantation.

Identification of Compounds Capable of Reducing or Inhibiting Transplant Arteriosclerosis The mouse of the invention and the methods of the invention can be used to screen compounds or other therapeutic approaches for the ability to inhibit the development of arteriosclerosis in a transplanted histoincompatible tissue. In such an assay, mice into which an allogeneic artery has been transplanted are treated, e.g., contacted with a candidate compound, or left untreated, i.e., no compound whatsoever is administered, or a vehicle alone is administered. As an internal control, a syngeneic artery may also be engrafted into the recipient mice. Alternatively, a syngeneic artery may be transplanted into a second mouse of the same strain as a control.

The transplanted arteries of treated and untreated animals are then evaluated at various time points for the development of arteriosclerosis, as described below. A reduction of neointimal thickening or other indication of transplant arteriosclerosis, e.g., infiltration of inflammatory cells or detection of actively proliferating cells, in the grafted arteries of treated mice compared to those of the untreated mice indicates that the candidate compound is efficacious in the treatment and/or prevention of the disease.

Methods of Evaluating Transplant Arteriosclerosis

Specimens of the transplanted arterial tissue can be prepared using standard histological methodology. For example, tissues can be set into paraffin or frozen prior to cutting into thin sections for microscopic evaluation.

Development of transplant arteriosclerosis, i.e., formation of a neointima, can be measured using methods well known in the art, e.g., immunohistochemical, histological, and morphometric techniques. Cellular responses involved in the graft rejection process can be identified by characterizing cell types, e.g., smooth muscle cells, leukocytes, macrophages, and subpopulations of T cells, e.g., $CD4^+$ T cells and $CD8^+$ T cells present in the neointima. The state of activation of cells in the neointima can also be evaluated by detecting PCNA, a marker of cell replication. The size, i.e., the area, of the neointima can also be measured.

Animals

Any two histoincompatible strains of mice can be used as the donor and recipient in the inventive model. The donor and recipient mouse may differ at any or all of the class I or class II major histocompatibility loci, or solely at one or more minor histocompatibility loci.

In the example described below, two strains of inbred mice were chosen for incompatibility in the H-2 region. B.10A(2R) ($H-2^{h2}$) mice were used as donors in the allograft group, and C57BL/6J ($H-2^b$) mice were used as donors in the isograft group. C57BL/6J ($H-2^b$) mice were used as recipients in both groups. All mice utilized were 28–32 g, 9 week old males, obtained from The Jackson Laboratory, Bar Harbor, Me.

EXAMPLE 1

Transplantation

The mouse of the invention was surgically modified as follows.

The surgical procedure was performed on anesthetized mice under a dissecting microscope (Wild model M3Z, Heerbrugg, Switzerland). The recipient mouse was fixed in a supine position with its neck extended. A midline incision was made on the ventral side of the neck from the suprasternal notch to the chin. The left carotid artery was dissected from the bifurcation in the distal end toward the proximal end as far as was technically possible. The artery was then occluded with two microvascular clamps (8 mm long, ROBOZ Surgical Instrument Co.), one at each end Two longitudinal arteriotomies (0.5–0.6 mm) were made using a fine needle (30 gauge) and scissors.

Figure 1:

In the donor mouse, both the left and the right carotid arteries were fully dissected from the arch to the bifurcation. Harvested arteries were preserved in isotonic saline at room temperature (5–10 minutes maximum for the first allograft and 30–40 minutes maximum for the second). The graft was then transplanted paratopically into the recipient in an end-to-side anastomosis with an 11/0 continuous nylon suture under 16× amplification (FIG. 1). Before the second (distal) anastomosis, the microvascular clamp at the proximal end was released temporarily (1–2 seconds) to flush away residual blood inside the lumen. Both clamps were released after the two anastomoses had been completed.

After clamp release, prominent pulsations were visible in both the transplanted loop and the native vessel. If there were no pulsations or if they diminished within a few minutes of restoration of blood flow, clot formation at the anastomosis was assumed and the procedure was terminated. If there were vigorous pulsations in the transplanted vessel, the skin incision was closed with a 4/0 interrupted suture. The grafts were subjected to 30–60 minutes of ischemia. Surgical success rate was routinely about 90%.

Grafts were harvested by cutting the transplanted loop from the native vessel at the suture lines. Allografts were harvested at 7, 15, and 30 days after transplantation. Isografts were harvested at 30 days only. The proximal half of the transplanted loop (about 2.5 mm) was fixed overnight in methyl Carnoy's fixative, and the other half was frozen in powdered dry ice and embedded in medium (Optimal Cutting Temperature Compound, Miles, Inc, Elkhart, Ill.). Histologic sectioning was begun at the center of the graft to avoid effects of the suture line.

Forty-two mice were used as recipients of 8 isografts and 34 allografts from 29 donor mice (some donors provided two arteries for transplantation). All 8 isografts were pulsating at the time of harvest and were included in the analysis.

Of the 34 allografts, 6 were not pulsating at the time of harvest and were thus omitted: one at day 7 (1/10), one at day 15 (1/10), and four at day 30 (4/14). Histologic examination revealed thrombosis in each case. After harvest of the transplanted arteries, two more allografts from day 7 were removed from the study. Even though these two grafts appeared to pulsate at the time of harvest, histologic examination revealed thrombosis. The day-30 allograft loops were thicker and whiter than the day-7 and day-15 loops, and showed diminished pulsations. There was no postoperative mortality.

Preparation of Tissue Samples for Analysis

Tissue samples in methyl Carnoy's fixative were processed for paraffin embedding in an automated system (Hypercenter XP, Shandon Scientific Ltd, Cheshire, England). Four-micron cross sections were cut in a microtome (Jung Biocut model 2035, Leica, Deerfield, Ill.), rid of paraffin (by melting for 10 min at 60° C.), washed three times with xylene, and rehydrated in graded ethanol. Frozen specimens (stored at −80° C.) were cut to a thickness of six microns in a motor-driven cryotome (RMC model CMT-955A, Tucson, Ariz.) and fixed in cold acetone (−20° C. for eight minutes before immunostaining.

Immunohistochemical Analysis

Paraffin sections were evaluated as follows. Proliferating cells were detected with an anti-PCNA antibody (clone PC10, 3 µg/ml, Oncogen Science, Uniondale, N.Y.). Vascular smooth muscle cells were detected with an antibody against smooth muscle alpha actin (anti-$NH_2$-terminal decapeptide, clone 1A4, 1:400, Sigma Chemical, St. Louis, Mo.). Endothelial cells were detected with a rabbit anti-human von Willebrand factor antibody (Lot 128, 1:1000, DAKO, Carpinteria, Calif.). Leukocytes were identified with a purified rat anti-mouse CD45 antibody (clone 30F11.1, 1:1000, Pharmingen, San Diego, Calif.). Biotinylated donkey anti-rabbit antibody (RPN 1004, 1:2000, Amersham, Arlington Heights, Ill.) was used as a secondary antibody for von Willebrand factor, and biotinylated goat anti-mouse $IgG_{2a}$ antibody (RPN 1181, 1:100, Amersham) was used as a secondary antibody for PCNA and alpha actin.

In frozen sections of transplanted arteries, $CD8^+$ and $CD4^+$ lymphocytes were detected with a rat anti-mouse Ly-2 antibody (clone 53–6.7, 1:50, Pharmingen), and a rat anti-mouse L3T4 antibody (clone RM-4-5, 1:50, Pharmingen), respectively. CD11b$^+$ cells were detected with a mouse antibody to the C3bi receptor (MAC-1 antigen) (clone BMA MI/70.15.1, Accurate Chemical & Scientific Corp, Westbury, N.Y.). Biotinylated goat anti-rat IgG (H&L) (Lot A073-NI63A, 1:200, Southern Biotechnology Associates, Inc, Birmingham, Ala.) was used as a secondary antibody for detecting CD4, CD8, and CD11b.

All primary antibodies were applied for 1–2 hours in phosphate-buffered saline (PBS) with 1% bovine serum albumin (pH 7.4). All secondary antibodies were applied for 1 hour, followed by a 30 min. incubation with avidin-biotinylated enzyme complex (ABC) peroxidase (Elite Vectastain ABC kit, Vector Laboratories, Burlingame, Calif.) or ABC alkaline phosphatase (Vectastain ABC kit, Vector Laboratories). Nonspecific binding was blocked with normal goat serum (1:10, 20 minutes) before addition of the primary antibody. After addition of the secondary antibody, endogenous peroxidase was blocked with hydrogen peroxide in methanol (2%, 10 minutes). Following each antibody application, all sections were washed three times in PBS (five minutes each time). The analysis was performed at room temperature.

All sections were labeled by the indirect peroxidase technique according to the manufacturer's instructions (Elite Vectastain ABC kit) and developed in 3,3'-diaminobenzidine (DAB, Vector Laboratories), with the exception of those treated with antibody to alpha actin. These sections were labeled indirectly with alkaline phosphatase and developed with VectorRed (Vector Laboratories). Immunohistochemical slides were counterstained with methyl green, except those treated with antibody to alpha actin. Alpha actin-stained sections were counterstained with Verhoeff's stain for elastic tissue (without ponceau staining). Nuclei were counted after methyl green or hematoxylin staining.

Murine spleen tissue was used as a positive control for cell surface expression of CD4, CD8, and CD45. The epithelial crypts of murine small intestine were used as a positive control for PCNA, and native vessels were used as a positive control for alpha actin and von Willebrand factor. As negative controls, some sections were incubated in the absence of primary antibody.

Histology and Morphometry

Sections of transplanted arteries were viewed under a Nikon Labophot-2 microscope equipped with a Sony 3CCD camera and television monitor. The intima was defined as the region between the lumen and the internal elastic lamina. The media was defined as the region between the internal and external elastic laminae. Cell counts in the intima and media were expressed as the number of nuclei in the entire cross-section of the respective structure. The adventitia (outside the external elastic lamina) varied in size because of differences in surgical dissection. Thus, cell counts in the adventitia were expressed in relation to surface area.

Areas were measured from images obtained at 100× magnification (Odyssey confocal microscope, Noran Instruments, Middleton, Wis.) in a transmitted light mode, using the Image-1 software (Universal Imaging Corp, West Chester, Pa.) on an IBM AT. Area measurements were made on one section (treated with Verhoeff's elastin stain) from each of the 34 animals studied (26 allografted, 8 isografted), about 500 µm from the center of the graft. Areas were recorded in µm$^2$ (±SD). In the statistical analyses for differences in mean areas, the individual values for the area from each animal at each time point for the allografts (7, 15 and 30 days), and at day 30 for the isografts, were averaged.

In qualitative studies of the 34 animals, an additional 9 to 24 sections per animal were examined from the midpoint of the carotid artery loop to the suture line to determine the uniformity of the lesion and whether or not it was concentric. Similar qualitative studies were performed on 156 consecutive sections from one of the day-7 allografted animals, 177 consecutive sections from one of the day-15 allografted animals, and 204 consecutive sections from one of the day-30 allografted animals. The lesions were concentric in general and asymmetric on occasion, with only modest variations from section to section within a single animal. Near the anastomosis, however, there was greater proliferation of neointima and an increase in adventitial inflammatory infiltrates.

Nuclei were counted in 4-µm, hematoxylin-stained paraffin sections (one from each of the 34 animals) that were consecutive to the sections used for the area measurements described above. Values represent the mean ±SD for each of the 3 allograft groups (days 7, 15, and 30) and the 1 isograft group.

For the detailed immunohistochemical studies, representative sections were selected from 3 isografted vessels and 9 allografted vessels (3 at day 7, 3 at day 15, and 3 at day 30). Both paraffin and frozen sections were prepared from each of the 12 animals in this group. The paraffin sections (4 µm) were consecutive to those used for the area measurements and counting of nuclei. They were stained for alpha actin, PCNA, and CD45. The frozen sections (6 µm) were stained for CD4, CD8, and Mac-1. Like the sections used for the area measurements, the frozen sections were also cut approximately 500 µm from the center of the arterial loop. These sections were cut from a portion of the specimen that had not been fixed initially. Finally, single sections from 1 allografted animal at day 7, 1 at day 15, and 1 at day 30, and 1 isografted animal, were stained with antibody to yon Willebrand Factor.

Cells were counted on a television monitor with a hand-held electronic colony counter and were reported as total number of cells for intimal sections and medial sections (±SD), and as total number of cells per µm$^2$ (±SD) for adventitial sections. Where the number of cells stained with an antibody is given as a percentage, the denominator represents the total number of nuclei counted by hematoxylin staining.

Statistical analyses were performed on sets of area measurement data and nuclear counting data from 26 allografted mice and 8 isografted mice (one section from each animal for each of the two data sets). Immunohistochemical data were statistically analyzed in a selected group of 12 animals comprising 3 mice from each of the 3 time points studied in the allograft group and 3 mice from the isograft group. Six sections from each animal, stained for alpha actin, PCNA, CD45, CD4, CD8, and Mac-1, were analyzed.

When data were consistent with a multivariate normal distribution of errors (FIGS. 4 and 6), they were subjected to a multivariate analysis of variance (MANOVA) with one grouping factor (Day: 7, 15, or 30) and one repeated measures factor (tissue locus: intima, media, or adventitia). The P4V program of the BMDP Statistical Software package was used for this purpose. When the day MANOVA factor was significant, individual comparisons between durations (e.g. 7 days versus 30 days) were computed with the planned comparisons feature available in P4V. Because each trivariate observation comprised values for surface area, number of nuclei, and number of nuclei per unit area, there were three trivariate observations per data-table cell in the two-factor MANOVA. When the data were inconsistent with a multivariate normal distribution (FIG. 5), a univariate analysis of variance (ANOVA) was performed before individual comparisons, which were made only when the day ANOVA factor was significant.

This statistical strategy, an application of the "protected test" concept (Bock, *Multivariate Statistical Methods in Behavioral Research*, New York: McGraw-Hill, 1975:266–68, 422–23), afforded a measure of insurance against spurious differences due to multiple comparisons. The protected test allowed us to set the alpha level for statistical significance at P values lower than 0.05 for all comparisons. Error estimates were stated as standard deviations, and none of the data required transformation to achieve consistency with error distributions assumed to be normal.

Neointima

Figure 2A:
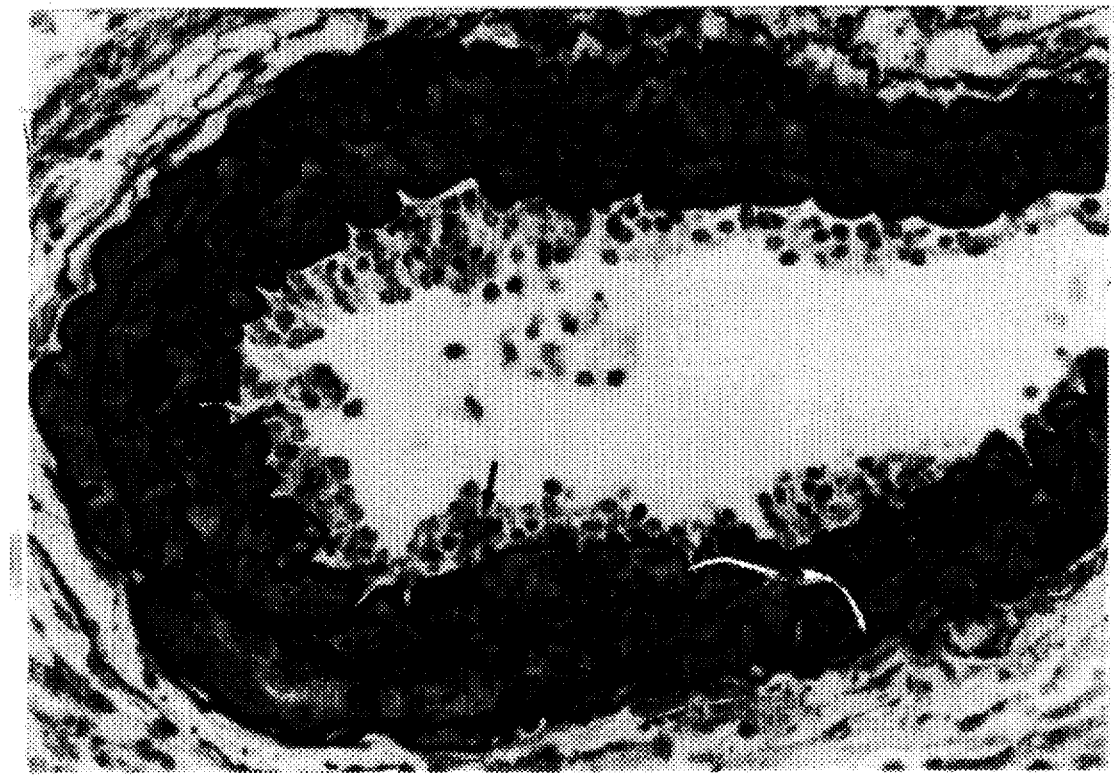
FIG. 2A is a photograph of a microscopic cross section of an allografted mouse carotid artery (7 days post-transplantation) stained for alpha actin (red). The arrow points to a cell positively stained for alpha actin.
Figure 2B:
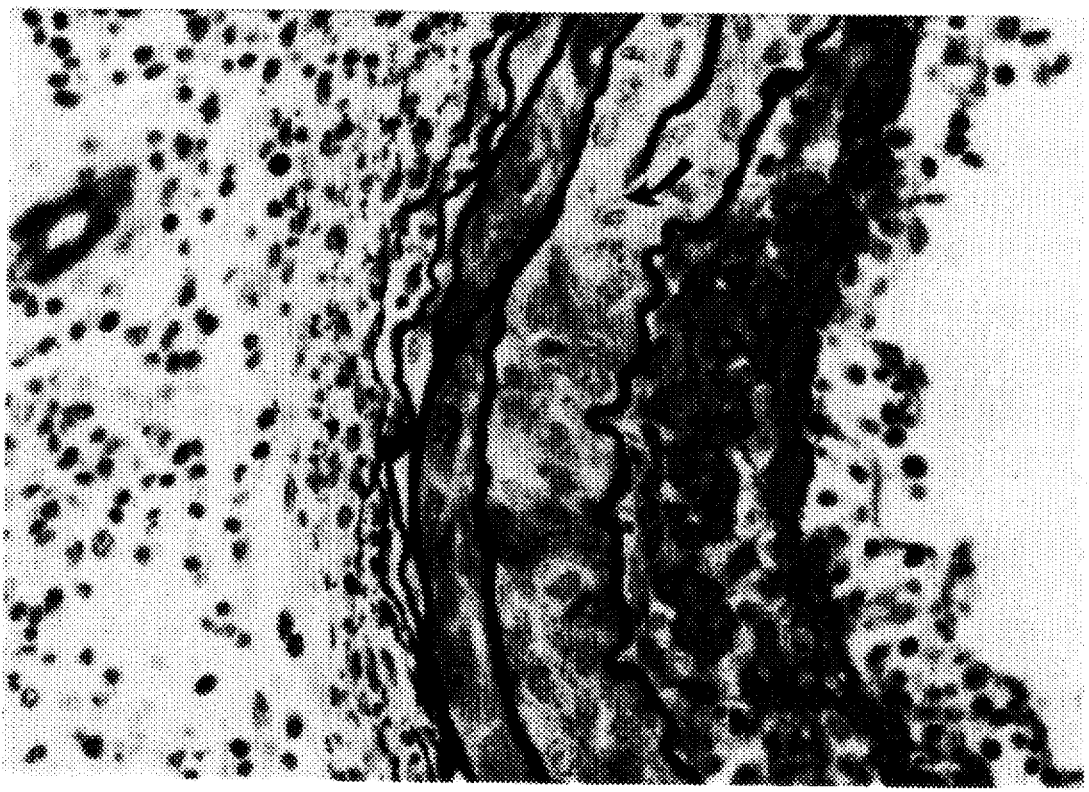
FIG. 2B is a photograph of a microscopic cross section of an allografted mouse carotid artery (15 days post-transplantation) stained for alpha actin (red). The arrow points to a break in the elastic lamina.
Figure 2C:
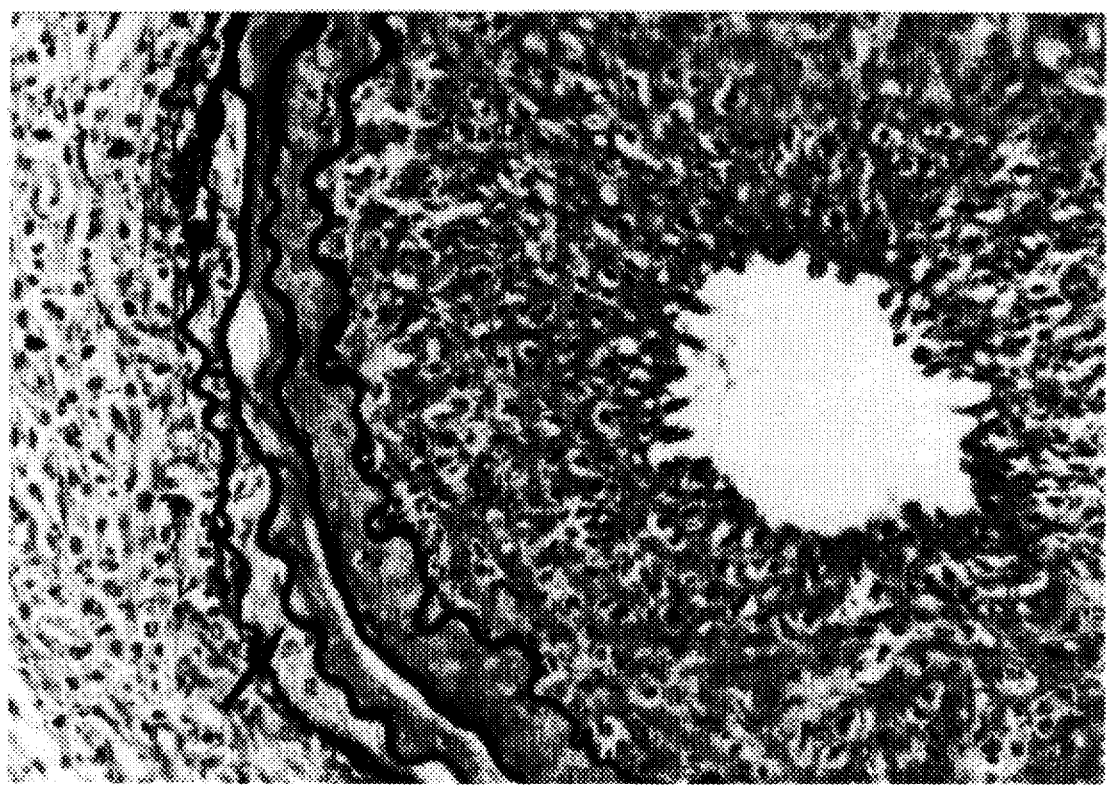
FIG. 2C is a photograph of a microscopic cross section of an allografted mouse carotid artery (30 days post-transplantation) stained for alpha actin (red). The arrow indicates the absence of medial cells staining for alpha actin.
Figure 2D:
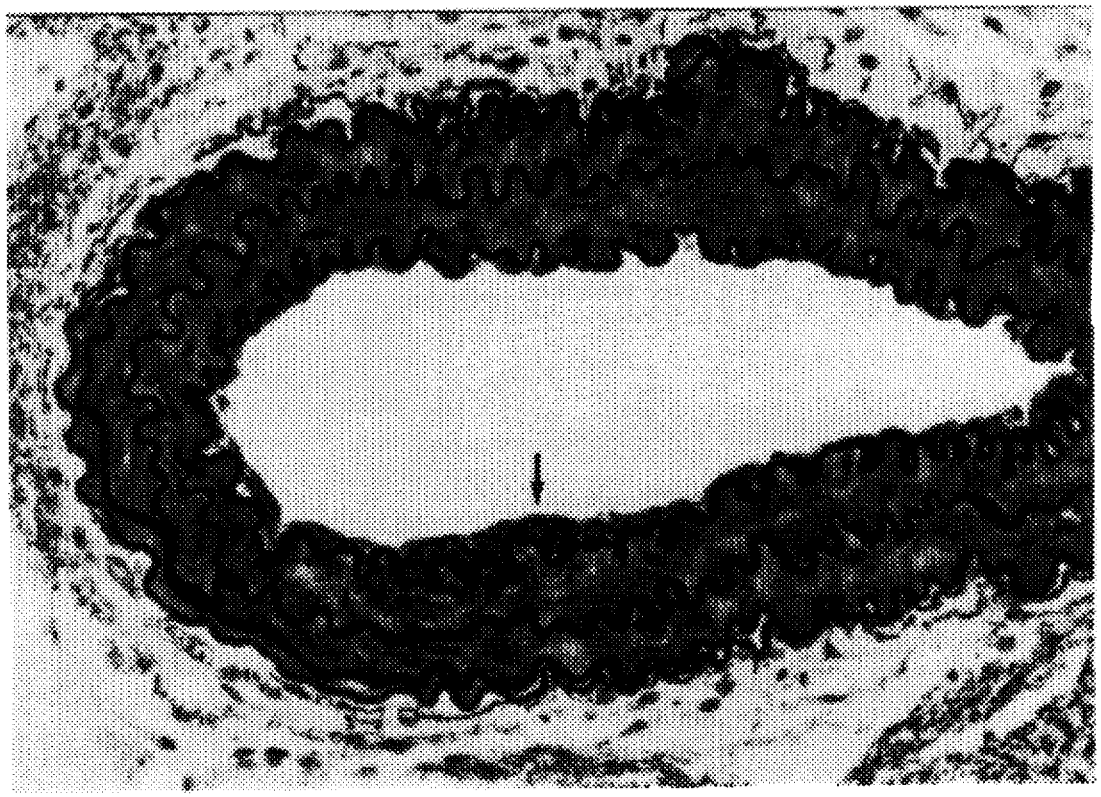
FIG. 2D is a photograph of a microscopic cross section of an isografted mouse carotid artery (30 days post-transplantation) stained for alpha actin (red).
Figure 2E:
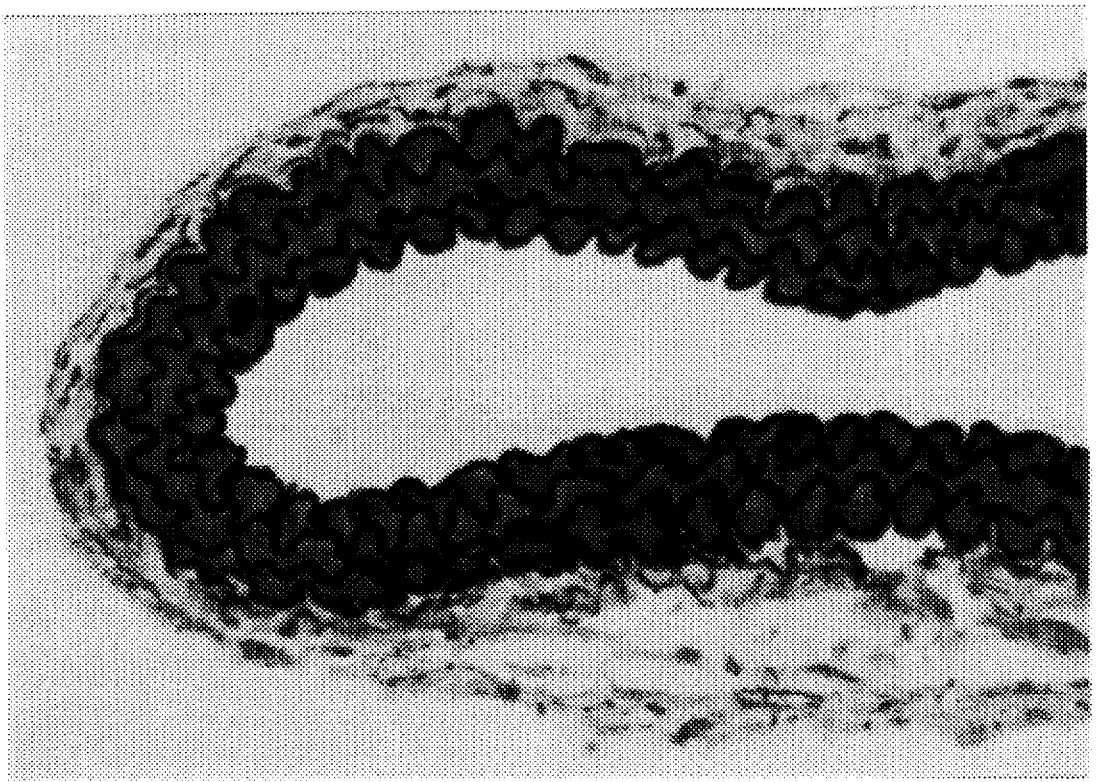
FIG. 2E is a photograph of a microscopic cross section of a native mouse carotid artery. The arrow points to a single layer of cells staining for alpha actin luminal to the internal elastic lamina.

FIGS. 2A–2C show typical histologic sections (stained for alpha actin) from allografted carotid arteries at 7, 15, and 30 days compared with sections from a 30-day isograft (FIG. 2D) and a native vessel (FIG. 2E). The day-7 allograft section (FIG. 2A) shows a 3-6-cell deep neointima that thickened rapidly by day 15 (FIG. 2B) and encroached upon most of the lumen by day 30 (FIG. 2C). In five of the ten day-30 allograft specimens, the neointima almost totally occluded the lumen. In contrast, the day-30 isograft section shows only a single layer of cells staining for alpha actin (FIG. 2D), luminal to the internal elastic lamina along only part of its circumference. This pattern was observed in two of the eight isograft specimens. Six other isograft specimens showed no evidence of neointima, and closely resembled the native vessel specimen (FIG. 2E).

There were few alpha actin-positive cells in the allograft neointima at day 7 (arrow, FIG. 2A). By day 15, about a third of the neointimal cells (those adjacent to the media) stained for alpha actin (FIG. 2B). By day 30, most of the cells in the neointima were alpha actin-positive (FIG. 2C).

FIG. 3A shows that about one third of the neointimal cells at day 7 stained for CD45, indicating that these cells were leukocytes. An examination of nuclear morphology indicated that most of these cells were mononuclear. By day 15, only the luminal part of the neointima stained for CD45 (FIG. 3B). A comparison between FIG. 3B and FIG. 2B revealed that the cells that did not stain for CD45 were alpha actin-positive. FIG. 3C shows that at day 15 there was abundant cellular proliferation among the luminal cells, as indicated by staining for PCNA. Some PCNA staining persisted at day 30 (FIG. 3D). Since most of the neointimal cells at day 30 were smooth muscle cells (positively staining for alpha actin), it is likely that these are the same cells that were PCNA-positive, i.e., smooth muscle cells were actively proliferating.

Area measurements and cell counting confirmed these visual observations of intimal change. Arteriosclerotic lesions in allografted arteries were generally concentric. The intimal area progressively increased, beginning at $10.31 \pm 5.14$ $\mu m^2$ at day 7 and extending to $28.82 \pm 20.78$ $\mu m^2$ (not significant) at day 15, and $68.3 \pm 23.4$ $\mu m^2$ at day 30 (P=0.0002, day 15 versus day 30). The difference in area between days 7 and 30 was also significant (P<0.0005) (FIG. 4A). The neointima showed a progressive increase in the number of nuclei, from $208 \pm 74$ at day 7 to $445 \pm 230$ at day 15 (P=0.025), and $783 \pm 217$ at day 30 (P=0.001, day 15 versus day 30) (FIG. 4B). Cell density (expressed as the number of nuclei per $\mu m^2$) decreased in the intima by day 30, a time when the intimal area was greatest (P=0.02) (FIG. 4C). This decrease in density suggests that matrix deposition is likely to account for some of the intimal thickening. At day 7, few cells in the intima stained for alpha actin, but by day 30, $80\% \pm 9\%$ of the cells were stained positively (P=0.0006) (FIG. 5A). At day 7, $29.5\% \pm 11.3\%$ of the intimal cells stained for CD45 (FIG. 5B). This amount decreased to $16.2\% \pm 2.2\%$ by day 30 (P=0.05). The percentage of cells in the intima that stained for PCNA reached a peak at day 15, $29.4\% \pm 5.7\%$, and decreased to $13.5\% \pm 4.0\%$ at day 30 (P=0.004) (FIG. 5C).

To resolve the identity of the leukocytes ($CD45^+$ cells) that made up most of the neointima at day 7, cell staining was carried out with antibodies to CD4, CD8, and CD11b. Most of the of cells at this time point were found to be $CD11b^+$ ($21.4\% \pm 7.3\%$). Because staining for CD11b cannot be used to differentiate macrophages and monocytes from granulocytes, nuclear morphology was examined. Most $CD11b^+$ cells had single-lobed rather than multi-lobed nuclei, indicating that they were macrophages or monocytes rather than granulocytes. Cells staining with antibodies to CD4 ($7.2\% \pm 5.2\%$ of nuclei) and CD8 ($11.1\% \pm 5.2\%$ of nuclei) were less abundant at day 7 than were cells staining for CD11b (P=0.05 for CD11b versus CD8 and P=0.007 for CD11b versus CD4). There was no significant difference between the prevalence of CD4 and CD8 cells at 7 days. There were no significant differences among the numbers of $CD11b^+$, $CD4^+$, and $CD8^+$ cells in the intima at later time points. None of these cells were found to be present in the media or adventitia at any time point. There were almost no detectable $CD11b^+$, $CD4^+$, or $CD8^+$ cells in the adventitia of the isograft at day 30.

Rapid formation of a neointima that progressed over 30 days to a nearly occlusive lesion was consistently observed in vascular allografts. The first cells to infiltrate the neointima appear to have been mononuclear leukocytes (by day 7). By day 15, these cells were joined by a large number of smooth muscle cells, and by day 30 most cells in the neointima were smooth muscle cells (which apparently continued to proliferate). The total number of cells continued to increase in the intima from day 7 to day 30, even though cell density decreased. This decrease in density appeared to be due to an increase in the extracellular matrix. This increase is likely to account for part of the increase in intimal thickness. Cellular proliferation appeared prominent among the mononuclear leukocytes at day 15 and among the smooth muscle cells at day 30. The initial mononuclear cell infiltrate was dominated by $CD11b^+$ cells, which, on the basis of nuclear form, appeared to be monocytes or macrophages. Helper and cytotoxic T cells were also present in the initial infiltrate.

Endothelium

Arteriosclerotic changes in the intima occurred without a loss of endothelium. FIG. 3E shows an intact endothelial layer (revealed by staining for von Willebrand factor) in a 30-day allograft with an exuberant neointima, and FIG. 3F shows a similarly intact endothelium in a 30-day isograft with a minimal neointima. These observations indicated that a neointimal lesion can occur without loss to the endothelial layer.

Media

At 7 days, alpha actin staining in the allograft media (FIG. 2A) was similar to that in the isograft at 30 days (FIG. 2D) and that in the native vessel (FIG. 2E). By day 15, alpha actin staining diminished in the media, and breaks in the elastic lamina became evident (FIG. 2B). At 30 days, there was a complete absence of alpha actin-positive cells in some regions of the media (FIG. 2C, arrow). These changes appeared to occur with infiltration of mononuclear leukocytes ($CD45^+$ cells) into the media at day 30. At days 15 and 30 (FIGS. 3C and 3D), a few PCNA-positive cells were detected in the media.

The cross-sectional area of the media did not differ significantly between the day-30 isograft and the day-7 allograft (FIG. 6A). There was a modest increase from 38.07±4.49 μm² to 53.47±8.90 μm² (P<0.0002) between day 7 and day 15, but no significant increase thereafter. There was no significant change with time in the number of nuclei in the media (FIG. 6B). Nuclear debris appeared in the media in some day-30 specimens.

Alpha actin-staining cells in the media decreased from nearly 100% at day 7 to 18%±12.6% at day 30 (P<0.00005) (FIG. 5A). Medial cells rarely stained for CD45 between days 7 and 15; the percentage of CD45⁺ increased approximately 10 fold to 14.2%±8.3% by day 30 (P=0.03) (FIG. 5B). The percentage of cells staining for PCNA in the media did not change significantly with time.

These observations indicated that medial smooth muscle cells were either lost or did not express alpha actin as the length of time the allograft resided in the recipient increased. Since the number of nuclei in the media did not change significantly, it is likely that smooth muscle cells were replaced by mononuclear leukocytes (as indicated by the late increase in the number of CD45⁺ cells in the media). The media of an isograft at 30 days was indistinguishable from that of a native vessel (by alpha actin staining).

Adventitia

Immunocytochemical quantification of adventitial cells is shown in Table 1. Each data point in the table represents the mean of three determinations ±SD.

Infiltration of CD45⁺ cells occurred in the adventitia at day 15 (FIG. 3B) and at day 30. The level of adventitial PCNA-positive cells increased significantly from day 7 to day 15 (1.65±0.08 to 4.16±1.1 nuclei/μm²) (P=0.003), but then dropped significantly at 30 days to a level no different from that observed at 7 days (0.92±0.14 nuclei/μm²) (P=0.0007) (see Table 1). CD45⁺ cells showed a similar pattern (see Table 1). The increase in CD45⁺ cells from day 7 to 15 was significant (P=0.0002), as was the drop from day 15 to day 30 (P=0.0006). Again, levels at 7 and 30 days were statistically indistinguishable. The isografts had few mononuclear cells in the adventitia. These observations indicate an early inflammatory response in the allograft adventitia involving mononuclear cells that proliferate.

TABLE 1

| Day | PCNA⁺ nuclei/μm² | CD45⁺ nuclei/μm² |
|---|---|---|
| 7 | 1.65 ± 0.08 | 0.77 ± 0.31 |
| 15 | 4.16 ± 1.1 | 2.74 ± 0.22 |
| 30 | 0.92 ± 0.14 | 1.10 ± 0.36 |

EXAMPLE 2

Allogeneic and syngeneic carotid transplants were carried out in the mouse strains indicated in Table 2 (and their appropriate controls) in order to define the role of an antigen-specific immune response and the participation of CD4⁺ and CD8⁺ T cells, B cells and humoral immunity, macrophages and natural killer (NK) cells. Each of these strains was tested for deletion of the cell type in question either by fluorescence-activated cell sorting of peripheral blood or by immunohistochemical examination of the spleen. In each case there was a marked reduction of the indicated cell type (Table 3).

The areas of the neointima and of the media of the experimental and control carotid arteries were measured by computerized planimetry. On serial section, intimal lesions were generally uniform in area from the center of the carotid loop until approximately 120, 5 micron sections from the suture line that defined the end of the transplanted segment. Measurements were reported at 30 microns and 60 microns from the center of the loop. In order to compensate for variations in overall vessel diameter among individual mice, the data were expressed as a ratio of intimal area/intimal+ medial areas. The results are shown in FIGS. 7A, 7B, and 8, which compare each of the mouse strains studied to their appropriate controls. FIGS. 9–13 shows representative microscopic sections of transplanted arteries stained for elastin so that the extent of the neointima as measured luminal to the internal elastic lamina may be seen.

TABLE 2

| Genotype | Lesion | Recipient Phenotype | Reference |
|---|---|---|---|
| Rag-2 Deletion | Absent rearrangement of TcR and Ig genes | Absence of antigen-specific cellular and humoral immune response | Shinkai, Y. et al. Cell 68:855 (1992) |
| MHC-I Deletion | Absent B₂ Microglobulin | Absent CD8(+) T cells | Koller et al. Science 241.1227 (1990) |
| MHC-II Deletion | MHC II A^β_α disrupted | Absent CD4(+) T cells | Grusby et al. Science 253:1417 (1991) |
| IgM CH₄ Deletion | Absent IgM receptor on pre-B cells | Absent B cells and humoral immune response | Kitamura et al. Nature 350:423 (1991) |
| Osteopetrosis homozygote | Absent macrophage colony stimulating factor | Reduced numbers of macrophages | Wiktor-Jedrzejcak et al. PNAS 87:4828 (1990) |
| Biege homozygote | Recessive mutation on chromosome 13 | Reduced numbers of natural killer cells | Roder & Duwe Nature 278:451 (1979) |

TABLE 3

2-Color Fluorescence-Activated Cell Sorting of Peripheral Blood Cells
Antibody (% Bright Cells)

| Mouse Strain | CD8 | CD4 | CD45 R/B 200 | NK 1.1 |
|---|---|---|---|---|
| C57B1/6 | 3.5 | 7.1 | 6.9 | 30.9 |
| 129xC57/B16 | 12.4 | 27.0 | 16.4 | 16.6 |
| Rag-2 Deletion | 0.2 | 0.1 | 2.4 | 30.7 |
| MHC-I deletion | 0.1 | 35.2 | 10.3 | 23.3 |
| MHC-II deletion | 12.4 | 1.3 | 19.6 | 36.2 |
| IgM CH₄ deletion | 4.8 | 25.3 | 3.7 | 51.1 |
| Osteopetrosis Homozygote | 9.7 | 17.6 | 18.7 | 20.7 |
| Beige homozygote | 7.7 | 17.7 | 33.7 | 6.3 |

It is apparent that Rag-2 deletion mice form essentially no neointima (see FIG. 8), indicating that in the absence of an immune response, transplant arteriosclerosis does not occur. Similarly, mice unable to mount a humoral immune response (transmembrane domain of mu chain deletion) manifest a minimal neointima, underlying the importance of specific antibody in the mediation of the arteriosclerotic response (FIG. 11). In mice with MHC Class II antigen deletion (FIG. 10) and in the OP/OP mice with MCSF deficiency and diminished macrophage numbers (FIG. 12), there is a significant reduction in the size of the neointima. Deletion of the MHC I gene (FIG. 9) or of natural killer cells (FIG. 13) had no effect, intimal lesions being no different from controls.

A specific immune response with the participation of $CD4^+$ T cells, macrophages and humoral antibody was found to be essential in the formation of transplant arteriosclerosis. $CD8^+$ T cells and natural killer cells appear not to be involved. These data suggest that in order for the process of transplant associated arteriosclerosis to occur, macrophages or B cells present antigen via MHC Class II antigens to CD4+ T cells. $CD4^+$ T cells in turn stimulate B cell proliferation via cytokines. B cells then produce specific humoral antibodies that activate macrophages via their Fc-I receptors. Macrophages, in turn, stimulate smooth muscle proliferation through paracrine stimulation by cytokines.

EXAMPLE 3

As discussed above, macrophages, humoral antibody, and $CD4^+$ T cells play a significant role in the formation of transplant-associated arteriosclerosis, whereas $CD8^+$ T cells and natural killer cells appear to be uninvolved. Therapeutic approaches, such as gene therapy, antisense therapy, ribozyme therapy, and antibody therapy may be used to inhibit the mechanisms involved the development of neointimal thickening.

Antisense therapy may be used to inhibit expression of proteins involved in the development of transplant arteriosclerosis. The antisense strand (either RNA or DNA) may be directly introduced into the cells in a form that is capable of binding to the mRNA transcripts. Alternatively, a vector-containing sequence which, which once within the target cells is transcribed into the appropriate antisense mRNA, may be administered. Antisense nucleic acids which hybridize to mRNA can decrease or inhibit production of the polypeptide product encoded by a gene by associating with the normally single-stranded mRNA transcript, thereby interfering with translation and thus, expression of the protein.

Ribozyme therapy can also be used to inhibit gene expression. Ribozymes bind to specific mRNA and then cut it at a predetermined cleavage point, thereby destroying the transcript. These RNA molecules may be used to inhibit expression of a gene encoding a protein involved in the formation of transplant arteriosclerosis according to methods known in the art (Sullivan et al., 1994, J. Invest. Derm. 103:85S–89S; Czubayko et al., 1994, J. Biol. Chem. 269:21358–21363; Mahieu et al, 1994, Blood 84:3758–65; Kobayashi et al. 1994, Cancer Res. 54:1271–1275).

Another therapeutic approach to inhibiting the expression of proteins or polypeptides involved in the development of transplant arteriosclerosis is the production of intracellularly expressed antibodies which, when expressed in a cell, bind to and prevent the transport and surface expression of target proteins. Intracellular antibodies may be expressed in a cell using known techniques (Chen et al., 1994, Hum. Gene Ther. 5:595–601) to inhibit cell surface proteins such as MHC Class II antigens or secreted proteins such as immunoglobulins.

A nucleic acid may be introduced into cells of a donor organ or directly into the mammalian recipient by standard vectors and/or gene delivery systems. Suitable gene delivery systems may include liposomes, receptor-mediated delivery systems, naked DNA, and viral vectors such as herpes viruses, retroviruses, adenoviruses and adeno-associated viruses, among others.

A therapeutic composition may include one or more compounds, e.g., nucleic acids or immunosuppressive agents, and a pharmaceutically acceptable carrier. The therapeutic composition may also include a gene delivery system as described above. Pharmaceutically acceptable carriers are biologically compatible vehicles which are suitable for administration to an animal: e.g., physiological saline. A therapeutically effective amount of a compound is an amount which is capable of producing a medically desirable result in a treated animal, e.g., inhibition of expression of a target gene, e.g., a cell surface or secreted protein, or inhibition of cell activity, e.g., proliferation, migration, antigen presentation, antibody production, or cytokine production.

Parenteral administration, such as intravenous, subcutaneous, intramuscular, and intraperitoneal delivery routes, may be used to deliver the compound, with intravenous administration being the preferred route. Dosages for any one patient depends upon many factors, including the patient's size, body surface area, age, the particular compound to be administered, sex, time and route of administration, general health, and other drugs being administered concurrently. Dosages of the compound to be administered will vary (doses of immunosuppressive agents are expected to be in the range of doses used for administration of other immunosuppressive agents known in the art). A preferred dosage for intravenous administration of nucleic acids is from approximately $10^6$ to $10^{22}$ copies of the nucleic acid molecule. Alternatively, the compound may be administered via a timed-release implant placed in close proximity to the engrafted organ.

Ex vivo treatment of the donor organ may be carried out by immersing the organ in a solution containing a compound or therapeutic composition, e.g., a nucleic acid (e.g., antisense sequence, coding sequence, or ribozyme) prior to transplantation. Alternatively, an organ may be perfused or electroporated with solution containing a therapeutic composition.

B Cells as a Therapeutic Target

Immunosuppressive compounds which inhibit the activity of B cells may be used to inhibit the formation of transplant arteriosclerosis in engrafted organs. For example, the immunosupressive drug, 15-deoxyspergualin (Nadler et al., 1992, Science 258:484–486; Nadler et al., 1993, Ann. N.Y. Acad. Sci. 696:412–414; Tepper et al, 1993, Ann. N.Y. Acad. Sci. 696:123–132; Sterbenz et al., 1993, Ann. N.Y. Acad. Sci. 685:205–6; Mazzucco et al., 1993, Ann. N.Y. Acad. Sci. 685:202–204; Tepper et al., 1993, Ann. N.Y. Acad. Sci. 685:136–147) may be administered to the recipient mammal according to methods known in the art, e.g., intravenously, to inhibit humoral immune responses. Other potential inhibitors of B cell activity may be tested for the ability to inhibit transplant arteriosclerosis using the screening assays of the invention. Such compounds may be administered as described above. The compound is preferably one which does not significantly suppress transplant rejection per se, though can be used in conjunction with such a drug.

Intracellular immunization using antibodies specific for target immunoglobulins, e.g., constant regions of graft-specific immunoglobulins, may be used to prevent the secretion of such immunoglobulins. Antisense therapy and ribozyme therapy may also be used to inhibit expression of such immunoglobulins.

Macrophages as a Therapeutic Target

Macrophages migrate to the site of the organ graft, colonize the graft and participate in the development of transplant arteriosclerosis. Therapeutic approaches can therefore be taken to inhibit the migration of macrophages to the graft site as well as to inhibit the activity of macrophages at the graft site. Antibodies specific for macrophage or monocyte chemoattractant proteins or migration proteins may be administered to the donor organ directly (ex vivo) or to the recipient mammal (in vivo) to inhibit macrophage migration to and colonization of the engrafted organ. The expression of macrophage proteins, e.g., galactose/N-acetyl galactosamine macrophage lectin (Russell et al., 1994 J. Clin. Invest. 94:722–730), monocyte chemoattractant protein-1 (Russell et al., 1993, Proc. Natl. Acad. Sci. U.S.A., 90:6086–6090; Brieland et al. 1993, Am. J. Respir. Cell. Mol. Biol. 98:300–305), macrophage inflammatory-1α, or macrophage chemoattractant protein-1β (Wang et al., 1993, J. Immunol. 150:3022–3029), may be inhibited using antisense therapy, ribozyme therapy, or intracellular antibody therapy. Expression of the galactose/N-acetyl galactosamine macrophage lectin ligand, galactose/N-acetyl galactosamine oligosaccharide, in the donor organ may also be inhibited using the gene therapy techniques described above. Antibodies to these proteins may be administered ex vivo or in vivo to inhibit receptor-ligand binding and therefore the activation of macrophage function, e.g., secretion of cytokines which stimulate smooth muscle cell proliferation, at the graft site. Other potential inhibitors of macrophage activity may be tested for the ability to inhibit transplant arteriosclerosis using the screening assays of the invention. Such compounds may be administered as described above.

CD4$^+$ T Cells as Therapeutic Targets

CD4$^+$ T cells but not CD8$^+$ T cells were found to be essential in the formation of transplant arteriosclerosis. Thus, selective immunosuppression of this T cell subset can be used to inhibit transplant arteriosclerosis. For example, soluble CD4 (Deen et al., 1988, Nature 331:82–84; Fisher et al., 1988, Nature 331:76–78; Hussey et al., 1988, Nature 331:78–81; Smith et al., 1987, Science 238:1704–1707; Traunecker et al., 1988, Nature 331:84–86) or CD4-immunoglobulin fusion proteins, e.g., CD4 fused to the Fc segment of IgG (European patent application EP 0394827A1), may be administered to the recipient mammal to inhibit CD4$^+$ T cell activity. Soluble CD4 and soluble CD4 fusion proteins may inhibit T cell activity by competing with the T cell-bound receptor and aborting its co-stimulatory activity.

Antisense therapy, ribozyme therapy, and intracellular antibody therapy may be used to inhibit donor organ expression of proteins involved in helper T cell function, e.g., MHC Class II antigens. Antibodies to MHC class II antigens can also be used to block receptor-ligand associations, e.g., block binding of MHC Class II molecules to T cell surface CD4, and therefore inhibit activation of CD4$^+$ T cells, which in turn reduces the formation of arteriosclerosis in the engrafted organ. Compounds which inhibit the activity of CD4$^+$ T cells in vitro may be identified using methods known in the art; these compounds may then be screened for the ability to inhibit the formation of a neointima using the claimed screening assays. Compounds found to have transplant arteriosclerosis inhibitory properties in the mouse model can then be administered either ex vivo or in vivo as described above to inhibit transplant arteriosclerosis in a recipient mammal.

Other Embodiments

The invention permits exploitation of the genetic resources of commercially available murine strains. Genetics of the mouse have been extensively characterized. As a result, a large number of mouse strains and murine cell lines that manifest specific gene mutations and deletions are available. The mouse of the invention and the assays of the invention may utilize mouse strains that have been subjected to targeted gene deletions. Thus, the mouse of the invention makes possible the elucidation of the detailed pathogenesis of transplant arteriosclerosis and the definition of events and/or molecules that may serve as targets for therapeutic intervention.

Mouse strains in which genes central to the immune system have been mutated are readily available. Such mouse strains can be used according to the invention to define the specific roles of those genes to the pathogenesis of the disease. For example, mice that do not express MHC class II antigens and lack CD4$^+$ T cells (Cosgrove et al., Cell, 1991, 66:1051–1066; Grusby et al., Science, 1991, 253:1417–1420) can be used to determine whether MHC class II antigen expression in the endothelial cells of transplanted vessels initiates the arteriosclerotic process. Similarly, mice that do not express MHC class I antigens (and lack CD8$^+$ T cells) (Zjilstra et al., Nature, 1990, 344:742–746; Koller et al., Science, 1990, 248:1227–1230), or that do not express both class I and class II antigens (and lack both CD4$^+$ and CD8$^+$ T cells) (Grusby et al., Proc. Natl. Acad. Sci. USA, 1993, 90:3913–3917) can be used to determine the role of MHC antigens in the development of transplant arteriosclerosis. Mice that have deficient macrophage function (Yoshida et al., Nature, 1990, 345:442–444), or those that lack B lymphocytes (nu) (Shultz et al., Ann. Rev. Immunol., 1987, 5:367–403) or natural killer cells (bg) (Shultz et al. supra) can be used to evaluate the cellular contribution to the development of an arteriosclerotic lesion. Mice that cannot rearrange the variable regions of immunoglobulins or T-cell receptors (Alt et al., Immunol. Today, 1992, 13:306–314) can also be used in accordance with the invention to study transplant arteriosclerosis.

Other embodiments are within the following claims.

What is claimed is:

1. A surgically modified mouse, comprising an artery isolated from a histoincompatible donor mouse, wherein the isolated artery is transplanted in an end-to-side or a side-to-side anastomosis to an endogenous artery of said surgically modified mouse, and wherein said transplanted artery exhibits transplant arteriosclerosis within 30 days of transplantation.

2. The surgically modified mouse of claim 1, further comprising a second artery isolated from a histocompatible donor mouse, wherein the second isolated artery is transplanted in an end-to-side or a side-to-side anastomosis to an endogenous artery of said surgically modified mouse.

3. The surgically modified mouse of claim 1, wherein said isolated artery and said endogenous artery are each a carotid artery.

4. The surgically modified mouse of claim 1, wherein said endogenous artery is a carotid artery.

5. The surgically modified mouse of claim 4, wherein said isolated artery is a femoral artery.

6. The surgically modified mouse of claim 4, wherein said isolated artery is an aortic artery.

7. The surgically modified mouse of claim 1, wherein said surgically modified mouse and said donor mouse have different major histocompatibility complex haplotypes.

8. The surgically modified mouse of claim 7, wherein said surgically modified mouse has an H-2$^b$ haplotype and said donor mouse has an H-2$^{k2}$ haplotype.

9. The surgically modified mouse of claim 8, wherein said surgically modified mouse is of the C57BL/6J strain and said donor mouse is of the B.10A(2R) strain.

10. The surgically modified mouse of claim 7, wherein said surgically modified mouse has an H-2$^{h2}$ haplotype and said donor mouse has an H-2$^b$ haplotype.

11. The surgically modified mouse of claim 10, wherein said surgically modified mouse is of the B.10A(2R) strain and said donor mouse is of the C57BL/6J strain.

12. A method for screening a candidate compound to determine whether said candidate compound reduces transplant arteriosclerosis, comprising:
   (a) transplanting into a first mouse of a first inbred strain, an artery isolated from a donor mouse of a second inbred strain which is histoincompatible with said first inbred strain in an end-to-side or a side-to-side anastomosis;
   (b) transplanting into a second mouse of said first inbred strain, an artery isolated from a donor mouse of said second inbred strain in an end-to-side or a side-to-side anastomosis;
   (c) administering to said first inbred strain said candidate compound after transplantation of said artery into said first mouse; and
   (d) comparing (1) the degree of arteriosclerosis in said artery of said first mouse which occurs within 30 days after transplantation, with (2) the degree of arteriosclerosis in said artery of said second mouse which occurs within 30 days after transplantation, wherein a lesser degree of arteriosclerosis in said artery of said first mouse is an indication that said candidate compound reduces transplant arteriosclerosis.

13. A method for screening a candidate compound to determine whether said candidate compound reduces transplant arteriosclerosis, comprising:
   (a) transplanting into a first mouse of a first inbred strain, an artery isolated from a donor mouse of a second inbred strain which is histoincompatible with said first inbred strain in an end-to-side or a side-to-side anastomosis, wherein said artery from said donor mouse has been treated with said candidate compound before transplantation of said artery into said first mouse;
   (b) transplanting into a second mouse of said first inbred strain, an artery isolated from a donor mouse of said second inbred strain in an end-to-side or a side-to-side anastomosis; and
   (c) comparing (1) the degree of arteriosclerosis in said artery of said first mouse which occurs within 30 days after transplantation, with (2) the degree of arteriosclerosis in said artery of said second mouse which occurs within 30 days after transplantation, wherein a lesser degree of arteriosclerosis in said artery of said first mouse is an indication that said candidate compound reduces transplant arteriosclerosis.

14. The method of claim 12 or claim 13, wherein said candidate compound is an inhibitor of macrophage activity.

15. The method of claim 12 or claim 13, wherein said candidate compound is an inhibitor of CD4-positive T cell activity.

16. The method of claim 12 or claim 13, wherein said candidate compound is an inhibitor of B cell activity.

17. The method of claim 12 or claim 13, wherein said isolated artery from said first mouse and said second mouse are both carotid arteries.

18. The method of claim 12 or claim 13, wherein said isolated artery from said first mouse and said second mouse are both aortic arteries.

19. The method of claim 12 or claim 13, wherein said first inbred strain has a different major histocompatibility complex haplotype than said second inbred strain.

20. The method of claim 19, wherein said first inbred strain has an H-2$^b$ haplotype and said second inbred strain has an H-2$^{h2}$ haplotype.

21. The method of claim 20, wherein said first inbred strain is C57BL/6J, and said second inbred strain is B.10A (2R).

22. The method of claim 19, wherein said first inbred strain has an H-2$^{h2}$ haplotype and said second inbred strain has an H-2$^b$ haplotype.

23. The method of claim 22, wherein said first inbred strain is B.10A(2R) strain, and said second inbred strain is C57BL/6J.

24. A method of making the surgically modified mouse of claim 1, comprising:
   (a) providing a first mouse of a first inbred strain;
   (b) isolating a donor artery from a second mouse of a second inbred strain being histoincompatible with first inbred strain; and
   (c) transplanting said isolated donor artery in an end-to-side or a side-to-side anastomosis to an endogenous artery of said first mouse.

25. The method of claim 24, wherein said donor artery and said endogenous artery are each a carotid artery.

26. The method of claim 24, wherein said endogenous artery is a carotid artery.

27. The method of claim 26, wherein said donor artery is a femoral artery or an aortic artery.

28. The method of claim 24, wherein said first inbred strain and said second inbred strain have different major histocompatibility complex haplotypes.

29. The method of claim 28, wherein said first inbred strain has an H-2$^b$ haplotype and said second inbred strain has an H-2$^{h2}$ haplotype.

30. The method of claim 29, wherein said first inbred strain is C57BL/6J, and said second inbred strain is B.10A (2R).

31. The method of claim 28, wherein said first inbred strain has an H-2$^{h2}$ haplotype and said second inbred strain has an H-2$^b$ haplotype.

32. The method of claim 31, wherein said first inbred strain is B.10A(2R), and said second inbred strain is C57BL/6J.

* * * * *